United States Patent
Frey et al.

(10) Patent No.: US 8,592,216 B2
(45) Date of Patent: Nov. 26, 2013

(54) LABELING PEPTIDES WITH TERTIARY AMINES AND OTHER BASIC FUNCTIONAL GROUPS FOR IMPROVED MASS SPECTROMETRIC ANALYSIS

(75) Inventors: Brian L. Frey, Madison, WI (US); April L. Jue, Madison, WI (US); Casey J. Krusemark, Woodside, CA (US); Lloyd M. Smith, Madison, WI (US); Joshua J. Coon, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 348 days.

(21) Appl. No.: 12/759,950

(22) Filed: Apr. 14, 2010

(65) Prior Publication Data

US 2010/0330680 A1 Dec. 30, 2010

Related U.S. Application Data

(60) Provisional application No. 61/169,623, filed on Apr. 15, 2009.

(51) Int. Cl.
*G01N 37/00* (2006.01)
(52) U.S. Cl.
USPC ............... 436/56; 436/86; 436/106; 436/112
(58) Field of Classification Search
None
See application file for complete search history.

(56) References Cited

U.S. PATENT DOCUMENTS

| | | | |
|---|---|---|---|
| 4,354,045 A | 10/1982 | Merger et al. | |
| 5,961,991 A | 10/1999 | Wenke et al. | |
| 6,649,907 B2 | 11/2003 | Ebeling et al. | |
| 6,797,945 B2 | 9/2004 | Berggren et al. | |
| 6,872,575 B2 | 3/2005 | Regnier | |
| 6,906,322 B2 | 6/2005 | Berggren et al. | |
| 7,078,679 B2 | 7/2006 | Westphall et al. | |
| 2005/0199804 A1 | 9/2005 | Hunt et al. | |
| 2008/0050833 A1 | 2/2008 | Smith et al. | |
| 2010/0068819 A1* | 3/2010 | Hoffmann | 436/86 |

FOREIGN PATENT DOCUMENTS

| | | | | |
|---|---|---|---|---|
| CS | 268639 B1 | 10/1988 | | |
| CS | 272135 B1 | 11/1988 | | |
| EP | 1429147 | * 6/2004 | ............ | G01N 33/68 |
| EP | 1512679 A1 | 3/2005 | | |
| GB | 1383127 | 2/1975 | | |

(Continued)

OTHER PUBLICATIONS

Ashcroft, A.E., *Protein and peptide identification: the role of mass spectrometry in proteomics*. Natural Product Reports, 2003. 20(2):202-215.

(Continued)

*Primary Examiner* — Robert Xu
(74) *Attorney, Agent, or Firm* — Lathrop & Gage LLP

(57) ABSTRACT

The present invention provides methods for enhancing the fragmentation of peptides for mass spectrometry by modifying the peptides with a tagging reagent containing a functional group, such as a tertiary amine, having a greater gas-phase basicity than the amide backbone of the peptide. These high gas-phase basicity functional groups are attached to a peptide by reacting the tagging reagent to one or more available carboxylic acid groups of the peptide. Linking these high gas-phase functional groups to the peptides leads to higher charge state ions from electrospray ionization mass spectrometry (ESI-MS), which fragment more extensively during fragmentation techniques, particularly non-ergodic fragmentation techniques such as electron capture dissociation (ECD) and electron transfer dissociation (ETD).

22 Claims, 10 Drawing Sheets

(56) References Cited

FOREIGN PATENT DOCUMENTS

| | | |
|---|---|---|
| JP | 2005047840 | 2/2005 |
| WO | WO 2004/008480 | 1/2004 |
| WO | WO2004/070352 | 9/2004 |
| WO | WO2004/086050 | 11/2004 |
| WO | WO 2007/109292 | 9/2007 |
| WO | WO 2007/117665 | 10/2007 |

OTHER PUBLICATIONS

Barry, et al. *Use of S-pentafluorophenyl tris(2,4,6-trimethoxyphenyl)phosphonium acetate bromide and (4-hydrazino-4-oxo . . .* Rapid Commun. Mass spectrom.2003. 17:484-897.

Barry et al. *Derivatisation for liqu7id chromatography/electrospray mass spectrometry: synthesis of pyridinium . . .* Rapid Commun. Mass spectrom. 2003. 17:603-620.

Coon et al., *Tandem mass spectrometry for peptide and protein sequence analysis.* Biotechniques, 2005. 38(4): 519, 521, 523).

Coon et al., *Electron transfer dissociation of peptide anions.* Journal of the American Society for Mass Spectrometry, 2005. 16(6):880-882; Coon, J.J., et al., *Protein identification using sequential ion/ion reactions and tandem mass spectrometry.* Proceedings of the National Academy of Sciences of the United States of America, 2005. 102(27):9463-9468.

Cooper et al., *The role of electron capture dissociation in biomolecular analysis.* Mass Spectrometry Reviews, 2005. 24(2):201-222.

Domon et al., *Review—Mass spectrometry and protein analysis.* Science, 2006. 312(5771): 212-217.

Dongre et al., *Influence of peptide composition, gas phase basicity, and chemical modification on fragmentation efficiency: Evidence for the mobile proton model.* Journal of the American Chemical Society, 1996. 118(35):8365-8374.

Ge et al., *Top down characterization of larger proteins (45 kDa) by electron capture dissociation mass spectrometry.* Journal of the American Chemical Society, 2002. 124(4):672-678.

Good et al., *Performance characteristics of electron transfer dissociation mass spectrometry.* Molecular & Cellular Proteomics, 2007. 6(11):1942-1951.

Hegeman et al., *An Isotope Labeling Strategy for Quantifying the Degree of Phosphorylation at Multiple Sites in Proteins,* J. Am. Soc. Mass Spectrom. 2004. 15:647-653.

Ji et al., *Quantitative Proteome Analysis Using Differential Stable isotopic Labeling and Microbore LC-MALDI MS and MS/MS,* Journal of Proteome Research 2005. 4:734-742.

Ji et al.,*Differential Dimethyl labeling of N-Termini of Peptides after Guanidination for Proteome Analysis,* Journal of Proteome Research 2005 4:2099-2108.

Mann et al., *Analysis of proteins and proteomes by mass spectrometry.* Annual Review of Biochemistry, 2001. 70:437-473.

Mikesh et al., *The utility of ETD mass spectrometry in proteomic analysis.* Biochimica Et Biophysica Acta-Proteins and Proteomics, 2006. 1764(12):1811-1822.

Shadforth et al. *i-Tracker: For quantitative proteomi cs using iTRAQ (TM).* BMC Genomics 2005, 6:145.

Shortreed et al., *Ionizable Isotopic Labeling Reagent for Relative Quantification of Amine Metabolites by Mass Spectrometry,* Anal. Chem. 2006 78:6398-6403.

Swaney et al., *Supplemental activation method for high-efficiency electron-transfer dissociation of doubly protonated peptide precursors.* Analytical Chemistry, 2007. 79(2):477-485.

Syka et al., *Peptide and protein sequence analysis by electron transfer dissociation mass spectrometry.* Proceedings of the National Academy of Sciences of the United States of America, 2004. 101(26):9528-9533.

Wysocki et al., *Mass spectrometry of peptides and proteins.* Methods, 2005. 35(3):211-222.

Yi et al. *Increased quantitative proteome coverage with 13C/12C-based, acid-cleavable isotope-coded affinity tag reagent and modified . . .* Proteomics, 2005, 5:380-387.

Zhang et al., *N-Terminal peptide labeling strategy for incorporation of isotopic tags: a method for the determination of site-specific absolute phosphorylation stoichiometry,* Rapid Commun. Mass Spectrom. 2002 16:2325-2332.

Zhang et al., *Convergent syntheses of carbon-13 labeled midazolam and 1'-hydroxymidazolam,* Tetrahedron Letters 2005 46:2087-2091.

Zubarev et al., *Electron capture dissociation of multiply charged protein cations. A nonergodic process.* Journal of the American Chemical Society, 1998. 120(13):3265-3266.

Zubarev et al., *Towards an understanding of the mechanism of electron-capture dissociation: a historical perspective and modern ideas.* European Journal of Mass Spectrometry, 2002. 8(5):337-349.

Chrisman et al., *"Parallel Ion Parking: Improving Conversion of Parents to First-Generation Products in Electron Transfer Dissociation,"* Anal. Chem., May 15, 2005, 77(10):3411-3414.

Coon et al., *"Electron Transfer Dissociation of Peptide Anions,"* J. Am. Soc. Mass. Spectrom., Apr. 14, 2005, 16:880-882.

Frey et al., *"Ion-Ion Reactions with Fixed-Charge Modified Proteins to Produce Ions in a Single, Very High Charge State,"* Int J Mass Spectrom., Oct. 1, 2008, 276(2-3): 136-143.

Hsu et al., *"Stable-Isotope Dimethyl Labeling for Quantitative Proteomics,"* Anal. Chem., Nov. 8, 2003, 75:6843-6852.

Iavarone et al., *"Effects of Charge State and Cationizing Agent on the Electron Capture Dissociation of a Peptide,"* Anal. Chem., Apr. 15, 2004, 76(8): 2231-2238.

Jue et al., *"Enhancement of ETD fragmentation efficiency by a fixed-charge modification strategy,"* 55th ASMS Conference on Mass Spectrometry and Allied Topics, Indianapolis, Ind, Jun. 3-7, 2007, Session: Peptides: Fragmentation & Sequencing—126.

Jue et al., *"A fixed-charge modification strategy to enhance ETD-MS/MS fragmentation efficiency,"* 56th ASMS Conference on Mass Spectrometry and Allied Topics, Denver, CO, Jun. 1-5, 2008, Session: Peptides: Sequencing—420.

Krusemark et al., *"Global Amine and Acid Functional Group Modification of Proteins,"* Anal. Chem., Jan. 10, 2008, 80:713-720.

Lamos et al., *"Relative Quantification of Carboxylic Acid Metabolites by Liquid Chromatography—Mass Spectrometry Using Isotopic Variants of Cholamine,"* Anal. Chem., Jun. 12, 2007, 79:5143-5149.

Pitteri et al., *"Electron-Transfer Ion/Ion Reactions of Doubly Protonated Peptides: Effect of Elevated Bath Gas Temperature,"* Anal. Chem., Sep. 1, 2003, 77(17): 5662-5669.

Rooke et al., *"The Combination of Electron Capture Dissociation and Fixed Charge Derivatization Increases Sequence Coverage for O-Glycosylated and O-Phosphorylated Peptides,"* J. Am. Soc. Mass. Spectrom., Apr. 25, 2007, 18:1405-1413.

Frey et al. *"Enhancing ETD-MS/MS fragmentation efficiency by chemically modifying peptides,"* 6th Annual Uppsala Conference on Electron Capture and Transfer Dissociation, Dec. 7-10, 2008, Madison Wisconsin.

Xu et al., *"Mass Spectrometry Analysis of Phosphopeptides after Peptide Carboxy Group Derivatization,"* Anal. Chem., Sep. 27, 2008, 80:8324-8328.

\* cited by examiner

LABELING PEPTIDES WITH TERTIARY AMINES AND OTHER BASIC FUNCTIONAL GROUPS FOR IMPROVED MASS SPECTROMETRIC ANALYSIS

CROSS REFERENCE TO RELATED APPLICATIONS

This application claims the benefit of U.S. provisional application 61/169,623, filed Apr. 15, 2009; which is hereby incorporated by reference to the extent not inconsistent with the present disclosure.

STATEMENT REGARDING FEDERALLY SPONSORED RESEARCH OR DEVELOPMENT

This invention was made with United States government support awarded by the following agencies: National Institutes of Health HV028182, GM065406. The United States government has certain rights in this invention.

BACKGROUND OF THE INVENTION

Over the past few decades the art of protein sequence analysis has been propelled by advances in the field of mass spectrometry (Domon et al., *Review—Mass spectrometry and protein analysis*. Science, 2006. 312(5771): 212-217; Ashcroft, A. E., *Protein and peptide identification: the role of mass spectrometry in proteomics*. Natural Product Reports, 2003. 20(2):202-215; Mann et al., *Analysis of proteins and proteomes by mass spectrometry*. Annual Review of Biochemistry, 2001. 70:437-473; and Coon et al., *Tandem mass spectrometry for peptide and protein sequence analysis*. Biotechniques, 2005. 38(4): 519, 521, 523). At the core of these technologies is tandem mass spectrometry (MS/MS)—the process of peptide or protein ion dissociation with subsequent m/z analysis. As such, effective peptide ion fragmentation techniques are essential. The likelihood of successfully identifying a selected peptide or protein is primarily dependent upon the extent and quality of backbone fragmentation produced.

For years collision-activated dissociation (CAD) has been the primary method of implementing MS/MS. During CAD, a population of selected peptide cations undergoes collisions with an inert bath gas. The generated internal energy is distributed across the backbone of the peptide to induce cleavage of the weakest bonds (Zubarev et al., *Electron capture dissociation of multiply charged protein cations. A nonergodic process*. Journal of the American Chemical Society, 1998. 120(13):3265-3266). For peptide cations the protonated amide bonds are weakened and, in general, are favored for cleavage upon CAD. The CAD process, however, tends to fail in this regard when the target peptide contains: (1) a post-translational modification (PTM) that fragments through a lower energy pathway (e.g., phosphorylation, glycosylation, sulfonation, etc.), (2) certain amino acids, especially those that inhibit random protonation of the peptide backbone, and (3) more than ~15 amino acids (Dongre et al., *Influence of peptide composition, gas-phase basicity, and chemical modification on fragmentation efficiency: Evidence for the mobile proton model*. Journal of the American Chemical Society, 1996. 118(35):8365-8374; and Wysocki et al., *Mass spectrometry of peptides and proteins*. Methods, 2005. 35(3):211-222).

The shortcomings in tandem MS (i.e., CAD) can be eliminated by fragmentation technology using electron based dissociation methods, such as electron capture dissociation (ECD) or electron transfer dissociation (ETD). ECD and ETD are non-ergodic techniques that rely on either the capture or transfer of an electron to the peptide cation precursor to impart fragmentation (Zubarev et al., *Towards an understanding of the mechanism of electron-capture dissociation: a historical perspective and modern ideas*. European Journal of Mass Spectrometry, 2002. 8(5):337-349; Ge et al., *Top down characterization of larger proteins (45 kDa) by electron capture dissociation mass spectrometry*. Journal of the American Chemical Society, 2002. 124(4):672-678; Cooper et al., *The role of electron capture dissociation in biomolecular analysis*. Mass Spectrometry Reviews, 2005. 24(2):201-222; Syka et al., *Peptide and protein sequence analysis by electron transfer dissociation mass spectrometry*. Proceedings of the National Academy of Sciences of the United States of America, 2004. 101 (26):9528-9533; Coon et al., *Electron transfer dissociation of peptide anions*. Journal of the American Society for Mass Spectrometry, 2005. 16(6):880-882; Coon, J. J., et al., *Protein identification using sequential ion/ion reactions and tandem mass spectrometry*. Proceedings of the National Academy of Sciences of the United States of America, 2005. 102(27):9463-9468; and Mikesh et al., *The utility of ETD mass spectrometry in proteomic analysis*. Biochimica Et Biophysica Acta-Proteins and Proteomics, 2006. 1764(12):1811-1822).

Rather than using collisions, ETD reacts the selected peptide cations with anions of fluoranthene (or other negatively charged small molecules). This reaction proceeds by transfer of an electron from the fluoranthene anion to the peptide (an ion/ion reaction). The added electron causes the peptide to break randomly between each amino acid. Once the peptide is fragmented, the masses of each fragment are then recorded and used with the mass of the parent peptide to analyze the peptide. Unlike CAD, ETD causes cleavage of a different backbone bond to produce c and z-type fragment ions, rather than the b and y-type fragments generated by CAD. ETD can be considered a derivative of electron capture dissociation ECD which uses free electrons rather than anions to induce the same fragmentation pathways.

Whether performed in an ion cyclotron resonance cell of a Fourier transform mass spectrometer (FT-ICR-MS, ECD) or in a RF quadrupole ion trap (QIT, ETD), these electron based dissociation methods induce random backbone cleavage with little regard for the presence of PTMs, amino acid composition, or the number of amino acids in the sequence. Of course, the electron based methods are not without their own limitations. Early work employing ECD and recent large-scale experiments with ETD indicate that precursor cation charge density may be the most critical parameter in determining a successful sequencing outcome (Good et al., *Performance characteristics of electron transfer dissociation mass spectrometry*. Molecular & Cellular Proteomics, 2007. 6(11): 1942-1951). For ETD, percent fragmentation—defined as the number of observed c and z-type fragments divided by the number possible—decreases with increasing precursor residue per charge ratio. Since the amino acids have similar residue mass values and peptides are collections of amino acids, precursor mass-to-charge (m/z) can approximate the residue per charge ratio. Precursor peptide cations with m/z values above ~900—regardless of z—have a low probability of generating sufficient direct backbone fragmentation for sequence assignment.

Previous experiments have described attaching quaternary amines to peptides in order to increase the charge state for mass spectroscopy (published PCT application WO 2007/109,292, published on Sep. 27, 2007). While the quaternary amines successfully increased the charge state of the peptide, the resulting mass spectrometry spectra were too complex and chaotic to yield useful information. Additionally, tagging peptides with quaternary amines reduced the ability to purify the peptides by chromatography.

Previous experiments have also described techniques to coax the conversion of the non-dissociated EC/ET products to c and z-type fragments from precursor peptide cations (Swaney et al., *Supplemental activation method for high-efficiency electron-transfer dissociation of doubly protonated peptide precursors*. Analytical Chemistry, 2007. 79(2):477-485). One drawback of that approach is that the resultant products often undergo hydrogen atom rearrangement to render the c and z-type products either one Da lighter or heavier, respectively. These peaks are superposed onto the isotopic distributions of the directly produced ETD fragments and can be problematic during sequence assignment.

SUMMARY OF THE INVENTION

The present invention provides a method to enhance electron based fragmentation techniques for identification of target molecules, particularly peptides. The method is primarily based on a chemical labeling strategy that reacts a tagging reagent containing a tertiary amine or other functional group having high gas-phase basicity onto the target molecule. Alternatively, the tagging reagent contains a functional group comprising a protected amine, a phosphonium group or a sulfonium group. Preferably, the high gas-phase basicity functional groups are attached to a peptide by reacting the tagging reagent to one or more available carboxylic acid groups of the peptide.

The tagging reagents of the present invention comprise a binding group able to react with the target molecule and further comprise a functional group able to improve the fragmenting characteristics of the peptide once tagged. The binding group can be any group able to form a covalent bond with the target molecule. Preferably, the binding group is able to react with a carboxylic acid group of a peptide, and includes but not limited to primary and secondary amines. In one embodiment, the functional group of the tagging reagents comprise a tertiary amine, guanidine or other high gas-phase basicity functional group which has a greater gas-phase basicity than the amide backbone of a peptide to be identified and which is not a nucleophile at the time of attachment to the peptide. The high gas-phase basicity functional groups attach to the peptide through the reaction of the binding group of the tagging reagent with the carboxylic acid groups of the peptide. Modifying peptides with tertiary amines or other high gas-phase basicity groups leads to higher charge state ions from electrospray ionization mass spectrometry (ESI-MS). These more highly charged ions fragment more extensively during fragmentation techniques, particularly non-ergodic electron based dissociation techniques such as ETD. Other fragmentation methods such as ECD, which is also a non-ergodic fragmentation technique, and collision-induced dissociation (CID) also benefit from the higher charge states. The additional fragmentation leads to substantially more sequence information, which improves protein or peptide identification. In one embodiment, however, the tagging reagent does not comprise a quaternary amine.

In one embodiment, the present invention provides a method of ionizing a peptide having an amide backbone and one or more carboxylic acid groups, comprising the steps of providing the peptide; reacting at least a portion of the carboxylic acid groups of the peptide with a tagging reagent having a functional group having a greater gas-phase basicity than the amide backbone of the peptide, wherein the tagging reagent and one or more carboxylic acid groups react to link the functional group to the peptide to generate a labeled peptide, and wherein the functional group is not a nucleophile when the tagging reagent reacts with the one or more carboxylic acid groups; and ionizing the labeled peptide using electrospray ionization, thereby generating an ionized peptide. The functional groups of the labeled peptide increase the charge state of the ionized peptide compared to an unlabeled form of the peptide. In one embodiment, the functional group comprises a tertiary amine. In another embodiment, the functional group comprises a protected primary or secondary amine, a phosphonium, or a sulfonium group.

In a further embodiment, the present invention provides a method of analyzing a peptide having one or more carboxylic acid groups and an amide backbone, comprising the steps of providing the peptide; reacting at least a portion of the carboxylic acid groups with a tagging reagent having a functional group having a greater gas-phase basicity than the amide backbone of the peptide, wherein the tagging reagent and carboxylic acid groups react to link the functional group to the peptide, thereby generating a labeled peptide, and wherein the functional group is not a nucleophile when the tagging reagent reacts with the carboxylic acid groups; ionizing the labeled peptide using electrospray ionization, thereby generating an ionized peptide; fragmenting the ionized peptide; and analyzing the fragments of the ionized peptide. Using mass spectrometry, the one or more fragments can then be identified and quantified. Optionally, the method further comprises digesting a peptide precursor with proteolytic enzyme or chemical reagent thereby generating one or more peptides having a plurality of carboxylic acid groups. The tagging reagents may be reacted with the carboxylic acid functional groups prior to or after digestion. In one embodiment, the functional group of the tagging reagent comprises a tertiary amine. In another embodiment, the functional group comprises a protected primary or secondary amine, a phosphonium, or a sulfonium group.

The methods described herein may further comprise purifying the peptide or peptide precursor from a mixture, such as a cell lysate. The purification step may utilize any technique suitable for use with mass spectroscopy, such as liquid or gas chromatography techniques. Accordingly, the selected tagging reagent should be able to increase the charge state of the peptide while still allowing the peptide to be purified by techniques such as liquid chromatography. In one instance, twice as many peptides from a complex proteomics sample (a yeast cell lysate, for example) may be identified with this chemical tagging method compared to an unmodified sample.

The present invention also provides a composition comprising a tagged peptide wherein at least a portion of the aspartic acid and glutamic acid residues are modified to contain the high gas-phase basicity functional groups. Optionally, the C-terminus of the peptide is also modified to contain a tertiary amine. The modified peptide containing the high gas-phase basicity functional groups has a lower residue per charge ratio than the corresponding unmodified peptide. The peptide may be further modified so that at least a portion of the cysteine residues, lysine residues and/or N-terminus of the phosphopeptide are chemically blocked prior to reacting at least a portion of the carboxylic acid groups of the peptide with the tagging reagent. The tagged peptide may be a proteolytically digested protein, peptide or a fragment resulting from a proteolytic digestion. The peptides may be phosphopeptides or peptides modified to contain other functional groups.

Preferably, the tagged peptides which are ionized and fragmented are peptides having about 2 to about 100 amino acid residues, more preferably having about 5 to about 50 amino acid residues, more preferably having about 5 to about 25 amino acids, even more preferably having about 10 to about 20 amino acid residues. Proteins and large peptides identified and analyzed using the methods of the present invention are optionally digested into smaller peptides prior to fragmentation and ionization. The proteins and peptides can be digested using any enzyme or reagent known in the art, including, but not limited to, trypsin, chymotrypsin, Lys-C, Glu-C, Asp-N, Arg-C, pepsin, cyanogen bromide, and nitro-thiocyanobenzoic acid (cys NTCB). The protein or peptide may be digested prior to or after the tagging reagent has been reacted with the protein or peptide.

In one embodiment, the tagging reagent and carboxylic acids of the peptide react to link approximately 1 to 50 high gas-phase basicity functional groups to the peptide. Preferably approximately 1 to 20 high gas-phase basicity functional groups are linked to the peptide, more preferably approximately 1 to 10 high gas-phase basicity functional groups are linked to the peptide, or even more preferably approximately 2 to 5 high gas-phase basicity functional groups are linked to the peptide. Preferably, reacting the carboxylic acid groups of the peptide with the tagging reagent has a desired yield of tagged peptide of approximately 70% or greater, preferably approximately 85% or greater, preferably approximately 90% or greater, or even more preferably approximately 95% or greater.

The addition of a high gas-phase basicity functional group to the peptide as described herein increases the charge state of the ionized peptide and allows the tagged peptide to have a lower residue per charge ratio than the untagged peptide. In particular, this increases the fragmentation of the peptide during electron based dissociation techniques. The high gas-phase basicity functional groups of the tagging reagents are not nucleophiles at the time when the tagging reagent reacts with the carboxylic acids of the peptide. This ensures the functional group does not interfere with the reaction between the tagging reagent and carboxylic acid groups.

The tagging reagents of the present invention contain a functional group that has a gas-phase basicity greater than the amide backbone and that can form a positive charge with the addition of a proton. Alternatively, the functional group comprises a protected primary or secondary amine, a phosphonium, or a sulfonium group. In one embodiment, the functional group is a tertiary amine selected from the group consisting of aliphatic, heterocyclic aliphatic, aromatic, heterocyclic aromatic tertiary amines and combinations thereof. In another embodiment, the functional group is selected from the group consisting of guanidines, phosphoniums, sulfoniums, pyrrolidines, pyrrolines, morpholines, pyrrolidones, quinuclidines, anilines, pyridines, quinolines, imidazoles and combinations thereof having 30 carbon atoms or less, preferably having 20 carbon atoms or less, even more preferably having 10 carbon atoms or less.

In a further embodiment, the tagging reagents used herein contain a binding groups and a protected primary or secondary amine. The protecting groups can be any protecting group known in the art, including but not limited to BOC, Cbz, and FMOC protecting groups, and are removed after the tagging reagent has reacted with the peptide but prior to ionization and fragmentation. The protecting groups ensure the primary and secondary amines do not interfere with the reaction between the binding groups of the tagging reagent and the carboxylic acids of the peptide. Primary amines and secondary amines may have similar basicity to the tertiary amines used herein and may provide some advantages over tertiary amines in ETD fragmentation.

In addition, the tagging reagents of the present invention may contain one or more stable isotopes. For example, the tagging reagent may contain a heavy isotope of hydrogen, carbon, oxygen or nitrogen, such as deuterium, $^{13}C$, $^{18}O$, or $^{15}N$. In one embodiment, peptides are tagged with a mixture of an isotopically labeled tagging reagent (a heavy tag) and a tagging reagent that is not isotopically labeled (a light tag).

Isotopic tagging has a number of advantages. It improves the precision of relative quantification by minimizing or negating errors associated with run-to-run irreproducibility. Such errors can arise from variations in mass spectrometric detection sensitivity, such as those caused by ionization suppression in electrospray, or from retention time differences between runs. The isotopic pair of labeled compounds co-elute within a single run. Therefore, they have identical retention times and are electrosprayed from identical solution conditions.

Any reaction able to link the tagging reagent with the carboxylic acid groups of the peptide may be used; however, preferably the binding groups of the tagging reagent and carboxylic acid groups of the peptide react via an amidation reaction. In further embodiments, the reactions attaching the tertiary amine tagging reagents to the peptide are optimized to yield a nearly pure product after a simple three-step methodology. The three steps include blocking sulfhydryls in the peptide (such as cysteine residues), blocking amine groups in the peptide (such as lysine residues and the N-terminus), and then amidating the carboxylic acids of the peptide (such as aspartic and glutamic acid residues as well as the C-terminus). This reaction often yields conversion efficiencies in excess of 95% and the resultant tags are compatible with both ECD and ETD. Coupling reagents able to react the tagging reagent with the carboxylic acids include, but are not limited to, PyAOP, HATU, HBTU, BOP, AOP, PyBOP, DMT-MM and traditional carbodiimides such as DIC, DCC, and EDC. Moreover, tagged peptides digested with proteolytic enzymes or chemical reagents exhibit a substantially lowered residue/charge ratio resulting in the routine generation of high quality ETD-MS/MS spectra when applied to a simple mixture. Blocking sulfhydryls by reduction and alkylation is already performed almost universally for mass spectrometric analysis of proteins and peptides.

A benefit of this tagging methodology is that the carboxylic acid groups are blocked by the amidation reaction. This feature is especially advantageous for analyzing proteins and peptides having phosphate groups as post-translational modifications. These phosphopeptides are very important biologically and are the focus of many proteomics studies. Selective enrichment of phosphopeptides (from tryptic digests of phosphoproteins) often is performed with IMAC (immobilized-metal affinity chromatography), $TiO_2$, $ZrO_2$, or other phosphate selective enrichment techniques. Carboxylic acid groups can interfere with this procedure, especially for IMAC, and therefore are usually blocked by conversion to the methyl esters. The tagging methods provided herein additionally accomplish this blocking function. Furthermore, ETD is the preferred fragmentation mechanism for analyzing phosphopeptides because the phosphate group does not fall off, as often occurs during CID. Thus, a single labeling reaction performs two beneficial functions: it blocks the carboxylic acid groups to aid phosphate-selective purification, and it improves the ETD analysis due to the production of higher charge state ions.

DETAILED DESCRIPTION OF THE INVENTION

Definitions

Figure 1:
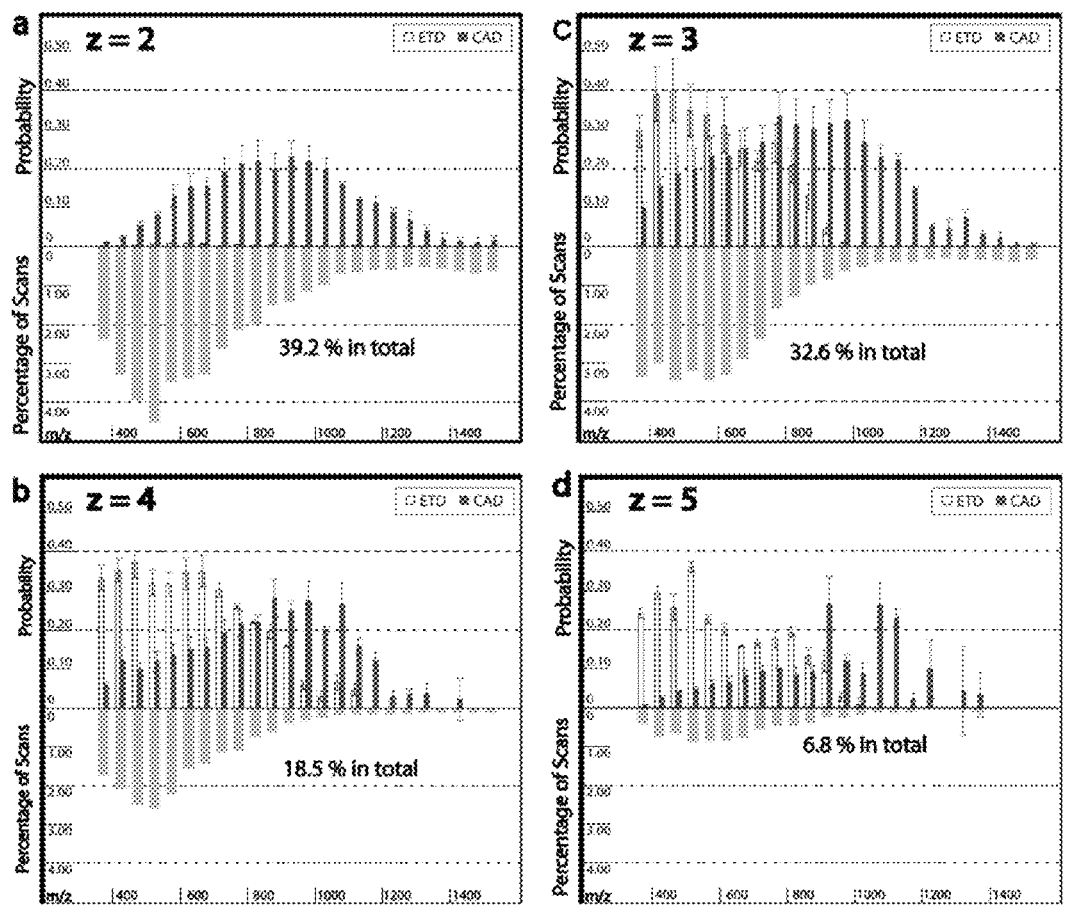
FIGS. 1a-1d shows the fragmentation efficiency of ETD and CAD for molecules having different charge and different m/z values.

The terms "peptide" and "polypeptide" are used synonymously in the present disclosure, and refer to a class of compounds composed of amino acid residues chemically bonded together by amide bonds (or peptide bonds). Peptides are polymeric compounds comprising at least two amino acid residues or modified amino acid residues. Peptides include compositions comprising a few amino acids and include compositions comprising intact proteins or modified proteins. Modifications can be naturally occurring or non-naturally occurring, such as modifications generated by chemical synthesis. Modifications to amino acids in polypeptides include, but are not limited to, phosphorylation, glycosylation, lipidation, prenylation, sulfonation, hydroxylation, acetylation, alkylation, acylation, carbamylation, iodination and the addition of cofactors. Peptides include proteins and further include compositions generated by degradation of proteins, for example by proteolytic digestion. Peptides and polypeptides may be generated by substantially complete digestion or by partial digestion of proteins. Identifying or sequencing a peptide refers to determination of is composition, particularly its amino acid sequence, and characterization of any modifications of one or more amino acids comprising the peptide or polypeptide.

"Protein" refers to a class of compounds comprising one or more polypeptide chains and/or modified polypeptide chains. Proteins may be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins may also include non-naturally occurring derivatives, analogues and functional mimetics generated by chemical synthesis. Exemplary derivatives include chemical modifications such as alkylation, acylation, carbamylation, iodination or any modification that derivatizes the protein. In the present invention, proteins may be modified by labeling methods, such as metabolic labeling, enzymatic labeling or by chemical reactions. Proteins may be modified by the introduction of stable isotope tags, for example as is typically done in a stable isotope dilution experiment. Proteins of the present invention may be derived from sources, which include but are not limited to cells, cell or tissue lysates, cell culture medium after cell growth, whole organisms or organism lysates or any excreted fluid or solid from a cell or organism.

"Fragment" refers to a portion of polymer analyte, such as a peptide. Fragments may be singly or multiple charged ions. Fragments may be derived from bond cleavage in a parent polymer, including site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond or combination of these processes. Fragments may refer to products formed by processes whereby one or more side chains of amino acids are removed, or a modification is removed, or any combination of these processes. Fragments useful in the present invention include fragments formed under metastable conditions or result from the introduction of energy to the precursor by a variety of methods including, but not limited to, collision induced dissociation (CID), surface induced dissociation (SID), laser induced dissociation (LID), electron capture dissociation (ECD), electron transfer dissociation (ETD), or any combination of these methods or any equivalents known in the art of tandem mass spectrometry. Fragments useful in the present invention also include, but are not limited to, x-type fragments, y-type fragments, z-type fragments, a-type fragments, b-type fragments, c-type fragments, internal ion (or internal cleavage ions), immonium ions or satellite ions. The types of fragments derived from a parent polymer analyte, such as a polypeptide analyte, often depend on the sequence of the parent, method of fragmentation, charge state of the parent precursor ion, amount of energy introduced to the parent precursor ion and method of delivering energy into the parent precursor ion. Properties of fragments, such as molecular mass, may be characterized by analysis of a fragmentation mass spectrum.

As used herein, "c-type" and "z-type" product ions refer to cleavage of peptides or polypeptides driven by free radical chemistry, such that the cleavage is directed to the N—Cα bond. The cleavage products are referred to as "product ions" or "fragments" that are classified as even-electron c-type fragments (N+H is even) and odd-electron z-type fragments (N+H is odd). Other common fragments or product ions, such as "b-type" and "y-type" product ions may also be generated.

"Ion" refers generally to multiply or singly charged atoms, molecules, and macromolecules having either positive or negative electric charge and to complexes, aggregates and clusters of atoms, molecules and macromolecules having either positive or negative electric charge. Ion includes cations and anions.

The term "alkyl" refers to a monoradical of a branched or unbranched (straight-chain or linear) saturated hydrocarbon and to cycloalkyl groups having one or more rings. Alkyl groups as used herein include those having from 1 to 30 carbon atoms, preferably having from 1 to 10 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups.

The term "alkenyl" refers to a monoradical of a branched or unbranched unsaturated hydrocarbon group having one or more double bonds and to cycloalkenyl groups having one or more rings wherein at least one ring contains a double bond. Alkenyl groups include those having 1, 2 or more double bonds and those in which two or more of the double bonds are conjugated double bonds. Alkenyl groups include those having from 1 to 20 carbon atoms, preferably having from 1 to 10 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

The term "alkynyl" refers to a monoradical of an unsaturated hydrocarbon having one or more triple bonds (C≡C) and to cycloalkynyl groups having one or more rings wherein at least one ring contains a triple bond. Alkynyl groups include those having from 2 to 20 carbon atoms, preferably having from 2 to 10 carbon atoms. Alkynyl groups include small alkynyl groups having 2 to 3 carbon atoms. Alkynyl groups include medium length alkynyl groups having from 4-10 carbon atoms. Alkynyl groups include long alkynyl groups having more than 10 carbon atoms, particularly those having 10-20 carbon atoms. The term "cycloalkynyl" refers to cyclic alkynyl groups of from 3 to 20 carbon atoms having a single cyclic ring or multiple condensed rings in which at least one ring contains a triple bond (C≡C). Descriptions herein with respect to alkynyl groups apply generally to cycloalkynyl groups. Alkynyl groups are optionally substituted. Substituted alkynyl groups include among others those which are substituted with alkyl, alkenyl or aryl groups, which groups in turn can be optionally substituted. Substituted alkynyl groups include fully halogenated or semihalogenated alkynyl groups, such as alkynyl groups having one or more hydrogens replaced with one or more fluorine atoms, chlorine atoms, bromine atoms and/or iodine atoms. Substituted alkynyl groups include fully fluorinated or semifluorinated alkynyl groups, such as alkynyl groups having one or more hydrogens replaced with one or more fluorine atoms.

The term "aryl" refers to a chemical group having one or more 5-, 6- or 7-member aromatic or heterocyclic aromatic rings. An aromatic hydrocarbon is a hydrocarbon with a conjugated cyclic molecular structure. Aryl groups include those having from 6 to 30 carbon atoms, preferably having from 6 to 18 carbon atoms. Aryl groups can contain a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocyclic aromatic group-containing groups corresponding to any one of the following benzene, naphthalene, naphthoquinone, diphenylmethane, fluorene, fluoranthene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed above provided in a covalently bonded configuration in the compounds of the present invention. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
—COOR where R is a hydrogen or an alkyl group or an aryl group and more specifically where R is methyl, ethyl, propyl, butyl, or phenyl groups all of which are optionally substituted;
—COR where R is a hydrogen, or an alkyl group or an aryl groups and more specifically where R is methyl, ethyl, propyl, butyl, or phenyl groups all of which groups are optionally substituted;
—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—N(R)$_2$ where each R, independently of each other R, is an alkyl group, acyl group or an aryl group and more specifically where R is methyl, ethyl, propyl, butyl, or phenyl or acetyl groups all of which are optionally substituted; or R and R can form a ring which may contain one or more double bonds.
—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
—OCOOR where R is an alkyl group or an aryl groups;
—SO$_2$N(R)$_2$ where R is a hydrogen, an alkyl group, or an aryl group and R and R can form a ring;
—OR where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

As used herein, the term "alkylene" refers to a divalent radical derived from an alkyl group or as defined herein. Alkylene groups in some embodiments function as attaching and/or spacer groups in the present compositions. Compounds of the present invention include substituted and unsubstituted $C_1$-$C_{30}$ alkylene, $C_1$-$C_{10}$ alkylene and $C_1$-$C_5$ alkylene groups. The term "alkylene" includes cycloalkylene and non-cyclic alkylene groups.

As used herein, the term "cycloalkylene" refers to a divalent radical derived from a cycloalkyl group as defined herein. Cycloalkylene groups in some embodiments function as attaching and/or spacer groups in the present compositions. Compounds of the present invention include substituted and unsubstituted $C_1$-$C_{30}$ cylcoalkenylene, $C_1$-$C_{10}$ cylcoalkenylene and $C_1$-$C_5$ cylcoalkenylene groups.

As used herein, the term "alkenylene" refers to a divalent radical derived from an alkenyl group as defined herein. Alkenylene groups in some embodiments function as attaching and/or spacer groups in the present compositions. Compounds of the present invention include substituted and unsubstituted $C_1$-$C_{20}$ alkenylene, $C_1$-$C_{10}$ alkenylene and $C_1$-$C_5$ alkenylene groups. The term "alkenylene" includes cycloalkenylene and non-cyclic alkenylene groups.

As used herein, the term "cylcoalkenylene" refers to a divalent radical derived from a cylcoalkenyl group as defined herein. Cycloalkenylene groups in some embodiments function as attaching and/or spacer groups in the present compositions.

As used herein, the term "alkynylene" refers to a divalent radical derived from an alkynyl group as defined herein. Alkynylene groups in some embodiments function as attaching and/or spacer groups in the present compositions. Compounds of the present invention include substituted and unsubstituted $C_2$-$C_{20}$ alkynylene, $C_2$-$C_{10}$ alkynylene and $C_2$-$C_5$ alkynylene groups. The term "alkynylene" includes cycloalkynylene and non-cyclic alkynylene groups.

As used herein, the term "halo" refers to a halogen group such as a fluoro (—F), chloro (—Cl), bromo (—Br) or iodo (—I).

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

As used herein, "sulfoniums" generally refer to a positive ion or monovalent radical containing three organic substituents, which can be different or the same, attached to a single atom of sulfur, and salts thereof. Tagging reagents of the present invention include sulfoniums having 1 to 20 carbon atoms, 1 to 10 carbon atoms, and 1 to 6 carbon atoms.

As used herein, "phosphoniums" generally refer to the ion $PH_4^+$, or corresponding organic derivatives of the type $RPH_3^+$, $(R)_2PH_2^+$ and $(R)_3PH^+$, where the organic substituents (R) can be different or the same, and salts thereof. Tagging reagents of the present invention include phosphoniums having 1 to 20 carbon atoms, 1 to 10 carbon atoms, and 1 to 6 carbon atoms.

As used herein, "guanidines" refer to a group of organic compounds having the general formula:

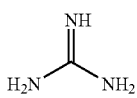

substituted with one or more alkyl, alkenyl, alkynyl or aryl groups, which in turn can also be optionally substituted as described above. Tagging reagents of the present invention include guanidines having 1 to 20 carbon atoms, 1 to 10 carbon atoms, and 1 to 6 carbon atoms.

As used herein, "pyrrolidines" refer to a group of organic compounds having the general formula:

substituted with one or more alkyl, alkenyl, alkynyl or aryl groups, which in turn can also be optionally substituted as described above. Tagging reagents of the present invention include pyrrolidines having 4 to 20 carbon atoms, 4 to 10 carbon atoms, and 4 to 8 carbon atoms.

As used herein, "pyrrolines" refer to a group of organic compounds having the general formula:

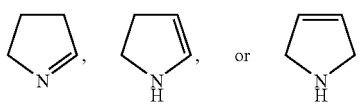

substituted with one or more alkyl, alkenyl, alkynyl or aryl groups, which in turn can also be optionally substituted as described above. Tagging reagents of the present invention include pyrrolines having 4 to 20 carbon atoms, 4 to 10 carbon atoms, and 4 to 8 carbon atoms.

As used herein, "pyrrolidones" refer to a group of organic compounds having the general formula:

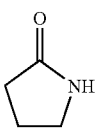

substituted with one or more alkyl, alkenyl, alkynyl or aryl groups, which in turn can also be optionally substituted as described above. Tagging reagents of the present invention include pyrrolidones having 4 to 20 carbon atoms, 4 to 10 carbon atoms, and 4 to 8 carbon atoms.

As used herein, "morpholines" refer to a group of organic compounds having the general formula:

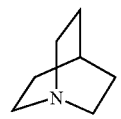

substituted with one or more alkyl, alkenyl, alkynyl or aryl groups, which in turn can also be optionally substituted as described above. Tagging reagents of the present invention include morpholines having 4 to 20 carbon atoms, 4 to 10 carbon atoms, and 4 to 8 carbon atoms.

As used herein, "quinuclidines" refer to a group of organic compounds having the general formula:

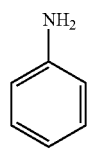

substituted with one or more alkyl, alkenyl, alkynyl or aryl groups, which in turn can also be optionally substituted as described above. Tagging reagents of the present invention include quinuclidines having 7 to 20 carbon atoms and 7 to 12 carbon atoms.

As used herein, "anilines" refer to a group of organic compounds having the general formula:

substituted with one or more alkyl, alkenyl, alkynyl or aryl groups, which in turn can also be optionally substituted as described above. Tagging reagents of the present invention include anilines having 6 to 20 carbon atoms and 6 to 10 carbon atoms.

As used herein, "pyridines" refer to a group of organic compounds having the general formula:

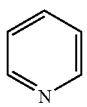

substituted with one or more alkyl, alkenyl, alkynyl or aryl groups, which in turn can also be optionally substituted as described above. Tagging reagents of the present invention include pyridines having 5 to 20 carbon atoms and 5 to 10 carbon atoms.

As used herein, "quinolines" refer to a group of organic compounds having the general formula:

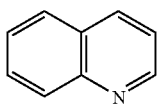

substituted with one or more alkyl, alkenyl, alkynyl or aryl groups, which in turn can also be optionally substituted as described above. Tagging reagents of the present invention include quinolines having 9 to 20 carbon atoms and 9 to 15 carbon atoms.

As used herein, "imidazoles" refer to a group of organic compounds having the general formula:

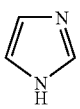

substituted with one or more alkyl, alkenyl, alkynyl or aryl groups, which in turn can also be optionally substituted as described above. Tagging reagents of the present invention include imidazoles having 3 to 20 carbon atoms and 3 to 10 carbon atoms.

As used herein, "tertiary amines" refer to amines of the type $(R)_3N$, with any combination of three different or the same alkyl, alkenyl, alkynyl or aryl substituents on the nitrogen atom. The alkyl, alkenyl, alkynyl or aryl groups can themselves be substituted as described above. "Aliphatic tertiary amines" refer to tertiary amines where the substituents are alkyl, alkenyl, or alkynyl groups. "Heterocyclic aliphatic tertiary amines" refer to aliphatic tertiary amines which form a ring structure in which at least one atom in the ring is carbon and at least one atom in the ring is an element other than carbon. "Aromatic tertiary amines" refer to tertiary amines where at least one of the substituents is an aryl group. "Heterocyclic aromatic tertiary amines" refer to aromatic tertiary amines where the amine nitrogen is part of the aromatic ring. Tagging reagents of the present invention include tertiary amines having 3 to 30 carbon atoms, 3 to 20 carbon atoms and 3 to 10 carbon atoms.

As used herein, "isotopically labelled", "isotopic", "isotopes", "isotope", "isotopically-different" and the like refer to compounds (e.g., tagging reagents, target analytes and end-products, etc.) whereby a process has introduced one or more isotopes into the relevant compound in excess of the natural isotopic abundance. "Isotopically-heavy" refers to a compound or fragments/moieties thereof that have been enriched with one or more high mass, or heavy isotopes (e.g., stable isotopes such as deuterium, $^{13}C$, $^{15}N$, and $^{18}O$).

"Gas-phase basicity" refers to the absolute or intrinsic basicity of a compound in the gas phase. It is expressed as the negative of the Gibbs energy ($\Delta Gr°$) change associated with the reaction: $B+H^+ \rightarrow B^+$—H. Similarly, pKa refers to the acid dissociation constant and is a quantitative measure of the strength of an acid, or conversely a base, in solution. It is believed tertiary amines and other functional groups having greater basicity are more easily ionizable and therefore would more likely achieve a higher charge state. As used herein, a high gas-phase basicity functional group refers to a functional group having a higher gas-phase basicity than the amide backbone of a peptide. In certain embodiments used herein, the tagging reagent functional group has a pKa range between 3 and 13, more preferably between 5 and 12.6, or a gas-phase basicity range between 840-1040 kJ/mol, more preferably between 880-1012 kJ/mol.

Tagging Peptides to Increase Charge State During Fragmentation

Non-ergodic, electron based fragmentation techniques, such as ETD, generally require a charge of z>2. Increased charge on the molecule will generally enhance fragmentation. Additionally, percent fragmentation—defined as the number of observed c-type and z-type fragments divided by the number of possible c-type and z-type fragments—decreases with increased residue per charge ratio (illustrated in FIG. 1). Since amino acids have similar residue mass values, mass-to-charge (m/z) can approximate the residue per charge ratio of the peptide. Peptide cations with m/z values above approximately 900 have a low probability of generating sufficient backbone fragmentation for sequence identity, regardless of z. As shown in FIG. 1, ETD fragmentation works best at m/z values below 800. Accordingly, it is desirable to modify the peptide to lower the residue per charge ratio in order to increase fragmentation.

In order to improve the charge density of peptides for electron based fragmentation methods, a tagging reagent having a high gas-phase basicity functional group is reacted with the carboxylic acid functional groups of one or more peptides prior to LC-MS/MS analysis. The tagging reagent can be added to a single isolated peptide or to multiple peptides in a complex mixture. Since the carboxylic acid functional group is prevalent in peptides, occurring at the C-terminus and among the side chain residues of a peptide, nearly all peptides will acquire one or more high gas-phase basicity functional groups as a result of the tagging reaction. By varying the gas-phase basicity of the appended functional group the amount of charge added during electrospray ionization and the subsequent residue per charge ratio can be regulated.

Tagging peptides with quaternary amines has previously increased the charge state of the peptide for mass spectrometry. However, the resulting spectra were sometimes too complex and chaotic to yield useful identification information. Additionally, tagging with quaternary amines led to reduced purification by chromatography. It is believed tagging peptides with tertiary amines and other functional groups of similar basicity instead of quaternary amines will also result in an increased charge state for the peptide but with clearer mass spectrometry results. It is further believed peptides tagged with high gas-phase basicity functional groups of the present invention will be better able to be purified by chromatography.

A high gas-phase basicity functional group, such as a tertiary amine, may be linked to a peptide using an amidation reaction such as illustrated below:

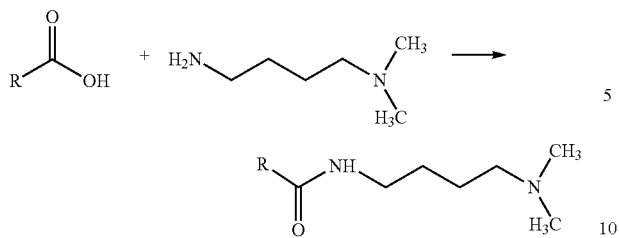

This reaction produces the desired product in high yield and keeps a likely charge site on the tagged peptide for fragmentation. Optionally, primary amines of the peptide, particularly the N-terminus, may additionally be converted to tertiary amines, such as reacting primary amines of the peptide with formaldehyde and pyridine-borane:

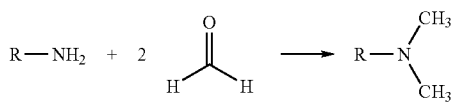

This reaction has shown to have over 99% efficiency and also results in an additional charge to the peptide.

Tertiary amine tagging reagents used herein contain a tertiary amine selected from the group consisting of aliphatic, aromatic, heterocyclic aliphatic, heterocyclic aromatic tertiary amines and combinations thereof. Alternatively, the tagging reagent functional groups are selected from the group consisting of sulfoniums, phosphoniums, guanidines, pyrrolidines, pyrrolines, morpholines, pyrrolidones, quinuclidines, anilines, pyridines, quinolines, imidazoles and combinations thereof.

Tagging reagents containing aliphatic tertiary amines have the formula (I):

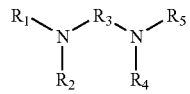

wherein, $R_1$ and $R_2$, independently of one another, are a hydrogen or a binding group which allows the binding group or a nitrogen attached to the binding group to react with a carboxylic acid;

$R_3$ is selected from the group consisting of branched and unbranched alkylene, alkenylene, and alkynylene groups having 1 to 10 carbon atoms, which are optionally substituted; and $R_4$ and $R_5$, independently of one another, are selected from the group consisting of hydrogen, and branched and unbranched alkyl, alkenyl and alkynyl groups having 1 to 10 carbon atoms, which are optionally substituted. Preferably, $R_3$ is an alkylene group having 2 to 5 carbon atoms. Preferably, $R_4$ and $R_5$, independently of one another, are alkyl groups having 1 to 3 carbon atoms. In one embodiment, $R_3$, $R_4$ and $R_5$ are not substituted.

Tagging reagents containing heterocyclic aliphatic tertiary amines have a formula selected from the group consisting of:

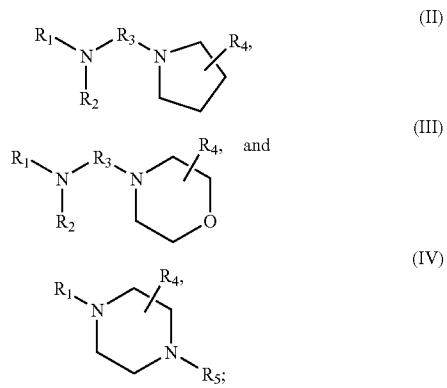

wherein, $R_1$ and $R_2$, independently of one another, are a hydrogen or a binding functional group which allows the binding group or a nitrogen attached to the binding group to react with a carboxylic acid;

$R_3$ is selected from the group consisting of branched and unbranched alkylene, alkenylene, and alkynylene groups having 1 to 10 carbon atoms, which are optionally substituted; and $R_4$ and $R_5$, independently of one another, are selected from the group consisting of hydrogen, and branched and unbranched alkyl, alkenyl and alkynyl groups having 1 to 10 carbon atoms, which are optionally substituted. Preferably, $R_3$ is an alkylene group having 2 to 5 carbon atoms. Preferably, $R_4$ and $R_5$, independently of one another, are alkyl groups having 1 to 3 carbon atoms. In one embodiment, $R_3$, $R_4$ and $R_5$ are not substituted.

Tagging reagents containing aromatic tertiary amines have the formula (V):

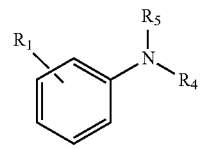

wherein, $R_1$ is a binding group which allows the binding group, such as an amino group, to react with a carboxylic acid;

$R_4$ and $R_5$, independently of one another, are selected from the group consisting of hydrogen, and branched and unbranched alkyl, alkenyl and alkynyl groups having 1 to 10 carbon atoms, which are optionally substituted. In one embodiment, $R_4$ and $R_5$, independently of one another, are alkyl groups having 1 to 3 carbon atoms. In a further embodiment, $R_4$ and $R_5$ are not substituted.

Tagging reagents containing heterocyclic aromatic tertiary amines have a formula selected from the group consisting of:

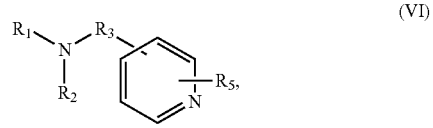

-continued

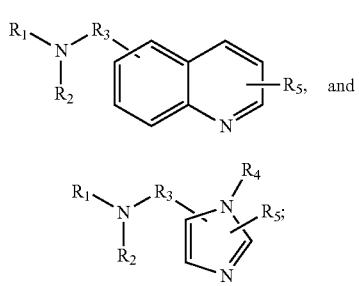

wherein, $R_1$ and $R_2$, independently of one another, are a hydrogen or a binding functional group which allows the binding group or a nitrogen attached to the binding group to react with a carboxylic acid;

$R_3$ is selected from the group consisting of branched and unbranched alkylene, alkenylene, and alkynylene groups having 1 to 10 carbon atoms, which are optionally substituted; and $R_4$ and $R_5$, independently of one another, are selected from the group consisting of hydrogen, and branched and unbranched alkyl, alkenyl and alkynyl groups having 1 to 10 carbon atoms, which are optionally substituted. Preferably, $R_3$ is an alkylene group having 2 to 5 carbon atoms. Preferably, $R_4$ and $R_5$ are both hydrogens. Optionally, $R_4$ and $R_5$, independently of one another, are alkyl groups having 1 to 3 carbon atoms. In another embodiment, $R_3$, $R_4$ and $R_5$ are alkylene or alkyl groups that are not substituted.

Alternatively, the tagging reagents used herein contain a guanidine group having the formula (IX):

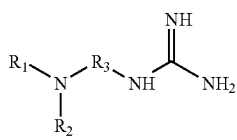

wherein, $R_1$ and $R_2$, independently of one another, are a hydrogen or a binding functional group which allows the binding group or a nitrogen attached to the binding group to react with a carboxylic acid; and $R_3$ is selected from the group consisting of branched and unbranched alkylene, alkenylene, and alkynylene groups having 1 to 10 carbon atoms, which are optionally substituted. Preferably, $R_3$ is an alkylene group having 2 to 5 carbon atoms. In one embodiment, $R_3$ is not substituted.

Alternatively, the tagging reagents used herein contain a protected amine group having the formula (X):

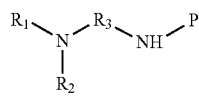

wherein, $R_1$ and $R_2$, independently of one another, are a hydrogen or a binding functional group which allows the binding group or a nitrogen attached to the binding group to react with a carboxylic acid;

$R_3$ is selected from the group consisting of branched and unbranched alkylene, alkenylene, and alkynylene groups having 1 to 10 carbon atoms, which are optionally substituted; and P is a protecting group that is removed after labeling as is known in the art but before ionization and fragmentation. The protecting groups can be any protecting group known in the art able to prevent the attached amine from interfering with the reaction between the binding groups of the tagging reagent and the carboxylic acids of the peptide. The protecting groups include, but are not limited to BOC, Cbz, and FMOC protecting groups. Preferably, $R_3$ is an alkylene group having 2 to 5 carbon atoms. In one embodiment, $R_3$ is not substituted.

The alkyl, alkenyl and alkynyl groups for the above formulas are optionally cyclic and/or substituted with functional groups which include but are not limited to, hydroxyl, amido, thiol, cyano, aromatic, alkoxy groups, and halogens, particularly fluorine. In some embodiments, the substituent is not chemically altered or functionalized during the reaction that attaches the tagging molecule to the carboxylic acid groups on the peptide. The substituent may be used to modify the pKa or basicity of the tertiary amine for creating optimal charge on the peptides. The substituent may also be used to improve other characteristics of the tagging reagent, such as solubility.

In addition, the tagging reagents of the present invention may contain one or more stable isotopes, such as deuterium, $^{13}C$, $^{15}N$, or $^{18}O$. In one embodiment, peptides from one sample are tagged with an isotopically labeled tagging reagent (a heavy tag) and peptides from another sample are tagged with a tagging reagent that is not isotopically labeled (a light tag). These samples are mixed together prior to mass spectrometric analysis, and the ratio of the peak intensities from the heavy- and light-labeled peptides reveals the relative amount of each peptide between the samples.

Relative quantification of heavy- and light-labeled molecules is accomplished by ratioing two peaks from a mass spectrum. The heavy and light forms are resolvable by the mass spectrometer. The resolution, R, of a typical mass spectrometer is defined by the equation: $R = m1/(m1-m2)$, wherein m1, is the mass of the heavy compound and m2 is the mass of the light compound. Relative quantification of the target molecule, T, using the isotopically-different labels, L and L*, follows the equation: $TL*/(TL*-TL) < R$, wherein TL is the mass of the light-labeled target molecule and TL* is the mass of the heavy-labeled target molecule. As can be appreciated, the minimum resolvable mass difference between a pair of isotopic labeled target molecules is generally a function of the mass of the target molecule and the resolution limit of the particular mass spectrometer used.

Hence, the mass difference between the heavy and light labels may be as small as 0.001 Dalton where the mass of TL is around 100 Dalton. The instant invention advantageously imparts small mass differences between heavy and light target molecules, such as where the heavy-labeled end-product has $^{13}C$, $^{15}N$, $^{18}O$ and/or $^2H$ and the light-labeled end-product has $^{12}C$, $^{14}N$, $^{16}O$ and/or $^1H$. The mass difference between such pairs of molecules is at least around 1 Dalton. Preferably, the instant labeling reagents create mass differences between heavy and light labeled target molecules of around 4 Daltons or more which advantageously eliminates or minimizes peak overlap arising from naturally-occurring isotopic variations in the target molecule.

EXAMPLES

The Examples set forth below illustrate certain embodiments of the invention. It is understood that the following Examples are not meant to limit the invention.

Example 1

Tagging Reagent Labeling Efficiency

To determine labeling efficiency, the tagging reagents provided in Table 1 below were reacted with different peptides having between 10 and 13 amino acid residues and containing two to five carboxylic acid functional groups in the form of the C-terminus, and aspartic acid (D) and glutamic acid (E) residues. The tagging reagents included tertiary amines (such as C3 methyl Tert as C5 methyl Tert as labeled in Table 1), a pyridine (C2 pyridine) and a quaternary amine (C4 methyl Quat).

TABLE 1

Structures of tagging reagents reacted with various peptides

C4 methyl Quat
4-(trimethylamine)butlylamine

C5 isopropyl Tert
N,N-diisopropyl-1,5-pentanediamine

C3 methyl Tert
3-(dimethylamine)propylamine

C3 morpholine
4-(3-aminopropyl)morpholine

C5 methyl Tert
5-(dimethylamine)amylamine

C2 morpholine
4-(2-aminoethyl)morpholine

C4 ethyl Tert
N,N-diethyl-1,4-butanediamine

C2 pyridine
4-(2-aminoethyl)pyridine

TABLE 2

Labeling efficiency

| | # of COOH Groups (D and E residues and the C-terminus) | Labeling Reagents | Reaction Efficiency |
|---|---|---|---|
| Test peptides | | | |
| pyroELYENKPRRPYIL | 2 | C4 methyl Quat | 98.8% |
| pyroELYENKPRRPYIL | 2 | C3 methyl Tert | 98.7% |
| pyroELYENKPRRPYIL | 2 | C5 methyl Tert | 98.8% |
| pyroELYENKPRRPYIL | 2 | C4 ethyl Tert | 99.3% |
| pyroELYENKPRRPYIL | 2 | C5 isopropyl Tert | 99.6% |
| pyroELYENKPRRPYIL | 2 | C3 morpholine | 99.8% |
| pyroELYENKPRRPYIL | 2 | C2 morpholine | 99.2% |
| pyroELYENKPRRPYIL | 2 | C2 pyridine | 98.8% |
| DAENLIDSFQEIV | 5 | C4 methyl Quat | 98.2% |
| DAENLIDSFQEIV | 5 | C3 methyl Tert | 99.4% |
| SDEEEAIVAYTL | 5 | C4 methyl Quat | 99.6% |
| SDEEEAIVAYTL | 5 | C3 methyl Tert | 99.5% |
| EQKLISEEDL | 5 | C4 methyl Quat | 97.7% |
| BSA digest peptides | | | |
| DAFLGSFLYEYSR | 3 | C4 methyl Quat | 99.0% |
| DAFLGSFLYEYSR | 3 | C5 methyl Tert | 99.4% |
| DDPHACYSTVFDK | 4 | C4 methyl Quat | 98.2% |
| DDPHACYSTVFDK | 4 | C5 methyl Tert | 98.5% |
| SLHTLFGDELCK | 3 | C4 methyl Quat | 98.5% |
| SLHTLFGDELCK | 3 | C5 methyl Tert | 96.7% |
| LVNELTEFAK | 3 | C4 methyl Quat | 98.7% |
| LVNELTEFAK | 3 | C5 methyl Tert | 97.7% |

Table 2 lists the reaction efficiency results from amidating different peptides with different tagging reagents. For example, the test peptide neurotensin (pyroELYENKPRRPYIL) gave ≥98.7% reaction efficiency for each of the eight amine labels. Note that this reaction efficiency is calculated as the percentage of acid groups on the peptide that were successfully derivatized. One may also wish to know the percentage of peptide that was completely modified; that value can be estimated from (% RxnEff÷100)$^n$, where n is the number of COOH sites on the peptide. For example, using the average reaction efficiency of 98.8% from all of the peptides listed in Table 2 gives 97.6% and 95.3% of completely modified peptide for n=2 and n=4, respectively.

The reaction efficiency per acid group appears to be independent of the number of acid sites, their position within the peptide, or the complexity of the peptide sample. Excellent efficiencies were obtained for test peptides having five acid groups, even when the acid-containing residues were clustered within the peptide (e.g. SDEEEAIVAYTL). Table 2 also lists results from amidation reactions performed on a more complex sample mixture, namely peptides from a tryptic digest of bovine serum albumin (BSA). The reaction efficiencies for the BSA digest peptides were mostly >98%, demonstrating that the amidation reaction proceeds nearly to completion even for complex peptide mixtures.

Example 2

Charge State Distributions for Modified and Unmodified Peptides

Tagging peptides with quaternary amines has successfully increased the charge state of the peptide for mass spectroscopy. However, the resulting spectra from certain peptides were too complex and chaotic to yield useful identification information. It is believed tagging the peptides with tertiary amines and compounds having similar gas-phase basicity instead of quaternary amines will also result in an increased charge state but with clearer mass spectrometry results.

Figure 2:
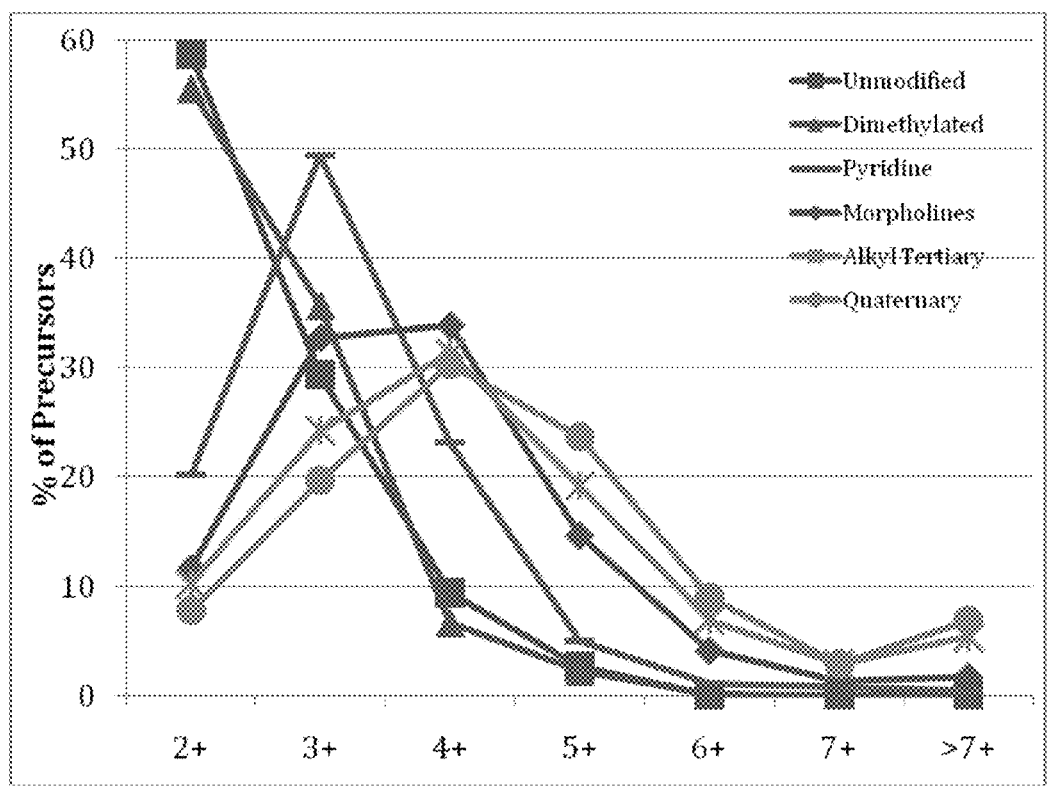
FIG. 2 shows the distribution of charge states from bovine serum albumin (BSA) digests obtained for unmodified and tagged peptides. As shown, nearly 90% of unmodified and dimethylated peptides had a charge state of 3 or less. In contrast, over 50% of peptides tagged with a quaternary amine, tertiary amine, or morpholine had a charge state greater than 3.

To test the effect of tagging peptides with different compounds, peptides from a BSA digest were methylated, left unmodified or tagged with a quaternary amine (C4 methyl Quat), alkyl tertiary amine (C3 methyl Tert, C5 methyl Tert, C4 ethyl Tert, or C5 isopropyl Tert), pyridine (C2 pyridine), or morpholine (C3 morpholine or C2 morpholine). FIG. 2 shows the distribution of charge states obtained for the various unmodified and modified peptides. These data were obtained by a comprehensive analysis of the peptide precursor charge states from LC-MS runs. The data include precursor mass values >250 m/z from a retention time window of 22-53 min.; these cut-offs were chosen to minimize the number of non-peptide precursors. The four aliphatic tertiary amine labels, and the two morpholine labels, were grouped together because they offered very similar charge state distributions. FIG. 2 shows how the low charge states of unmodified tryptic peptides (predominantly a charge state of +2) are converted to significantly higher charge states through labeling the peptides at their carboxylic acid sites. Furthermore, the increase in charge states correlates well with the increase in pKa, or more accurately the gas-phase basicity, of the amine label. The gas-phase basicity ranking is as follows: pyridine<morpholine<alkyl tertiary amine<quaternary amine.

The peptides tagged with the tertiary amines consistently had a lower charge state than the corresponding peptides tagged with the quaternary amine. This comparably lower charge state is potentially useful for mass spectrometry provided that the tertiary amine is still able to provide a charge state higher than the unmodified peptide.

The BSA digestion was performed after reduction with dithiothreitol and alkylation with iodoacetamide. Trypsin digestion proceeded in 8 M urea and 25 mM ammonium bicarbonate for 18 hours at 37° C. with a trypsin:protein ratio of approximately 1:20.

The peptides were amine-methylated by dissolving 0.1 mg of peptides in 50 µL of 1:1 methanol:water with 40 mM formaldehyde, 50 mM N-methylmorpholine, and 60 mM pyridine-borane. After reacting for 1 hour, the solution was vacuum-centrifuged to dryness. Acid amidation of the 0.1 mg of amine-methylated peptides occurred in 60 µL of dimethyl sulfoxide, to which was added a mixture of 5 µL of water, 2.6 µL of N-methyl morpholine, and 50 µmoles of quaternary or tertiary amine (e.g. 6.4 mg of C4-cholamine dihydrochloride). After vortexing, 2.1 mg of PyAOP was added and the reaction was allowed to proceed at room temperature for 2 hours.

Example 3

Charge States of Tagged Peptides from Yeast Lysates

Figure 3:
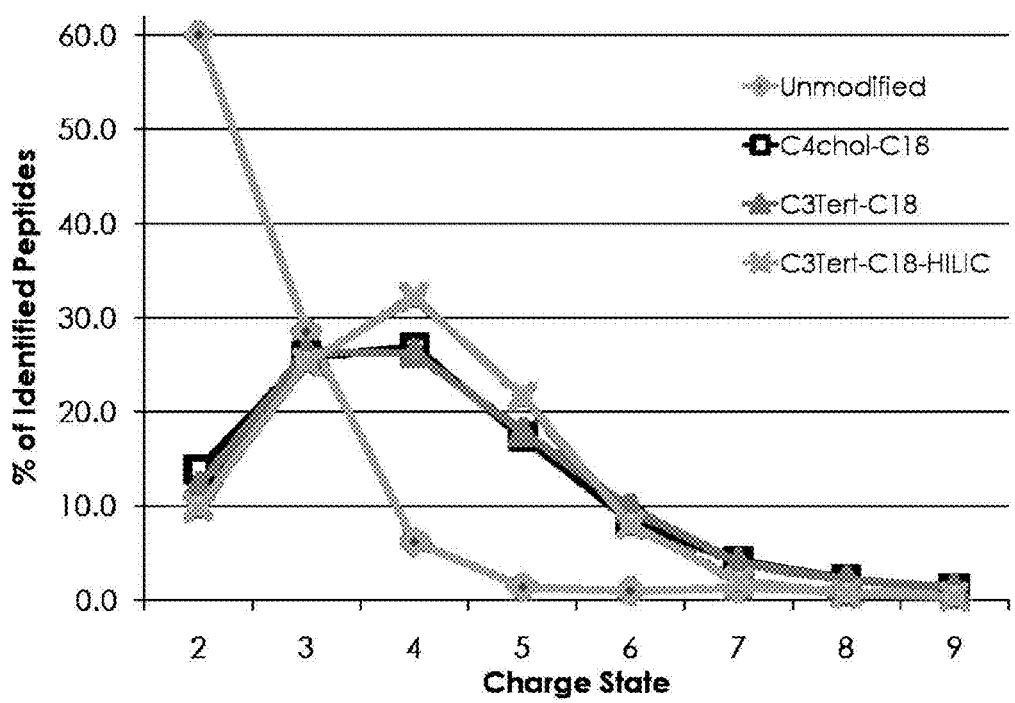
FIG. 3 shows the percentage of peptides from yeast lysate digests having particular charge states. As shown, nearly 90% of unmodified peptides had a charge state of 3 or less. In contrast, over 50% of peptides tagged with a quaternary amine or tertiary amine had a charge state greater than 3.

In another experiment, peptides resulting from the digest of yeast lysates by trypsin were tagged with C4-cholamine (purified on a C18 column), C3tert amine (purified on a C18 column), C3tert amine (purified on a C18 column and by HILIC), or left unmodified. FIG. 3 shows the percentage of these peptides having particular charge states. As shown in FIG. 3, nearly 90% of unmodified peptides had a charge state of 3 or less, with approximately 60% of the unmodified peptides having a charge state of 2. In contrast, over 50% of peptides tagged with the quaternary amine or tertiary amines had a charge state greater than 3. Thus the tertiary amine tags were able to successfully increase the charge state of the peptides similar to the quaternary amine.

Digestion of the yeast lysate was performed after reduction with dithiothreitol and alkylation with iodoacetamide. Trypsin digestion proceeded for 18 hours at pH 8 in 1 M guanidine hydrochloride with a trypsin:protein ratio of 1:20.

The peptides were amine-methylated by dissolving 0.1 mg of peptides in 50 µL of 1:1 methanol:water with 40 mM formaldehyde, 50 mM N-methylmorpholine, and 60 mM pyridine-borane. After reacting for 1 hour, the solution was vacuum-centrifuged to dryness. Acid amidation of the 0.1 mg of amine-methylated peptides occurred in 60 µL of dimethyl sulfoxide, to which was added a mixture of 5 µL of water, 2.6 µL of N-methyl morpholine, and 50 µmoles of quaternary or tertiary amine (e.g. 6.4 mg of C4-cholamine dihydrochloride). After vortexing, 2.1 mg of PyAOP was added and the reaction was allowed to proceed at room temperature for 2 hours.

Example 4

Charge States of Peptides Tagged with Different Tertiary Amines

Figure 4:
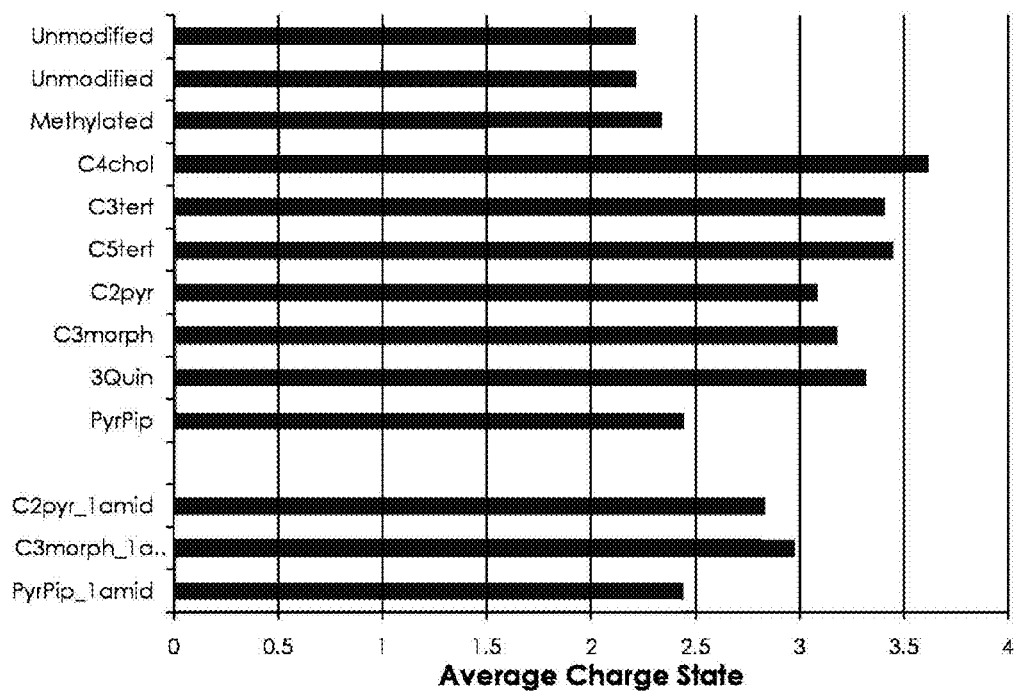
FIG. 4 shows the average charge state of neurotensin peptides that are unmodified, amine-methylated, and modified with various quaternary or tertiary amines.

Neurotensin is a 13 amino acid peptide neurotransmitter with a pyroglutamic acid residue at its N-terminus (pyroELYENKPRRPYIL). FIG. 4 shows the average charge state of neurotensin peptides that are unmodified or modified with various amines. The modifying reagents were the following: (4-aminobutyl)trimethylammonium chloride (C4chol), 3-(dimethylamino) propylamine hydrochloride (C3tert), 5-(dimethylamino)pentylamine (C5tert), 4-(2-aminoethyl) pyridine (C2pyr), 4-(3-aminopropyl)morpholine (C3 morph), 3-amino quinuclidine (3Quin), and 1-(2-pyrimidyl) piperazine dihydrochloride (PyrPip). Peptides tagged with a quaternary amine (C4-cholamine) resulted in the highest average charge state. Peptides tagged with a tertiary amine had a lower average charge state than the quaternary amine, but higher than the unmodified or amine-methylated versions of the peptides. Many of the tertiary amine peptides significantly increased the charge state of the peptide (an increase greater than 0.5) compared to the unmodified peptides, while other tertiary amines resulted in only a slight increase in the average charge state.

Figure 5:
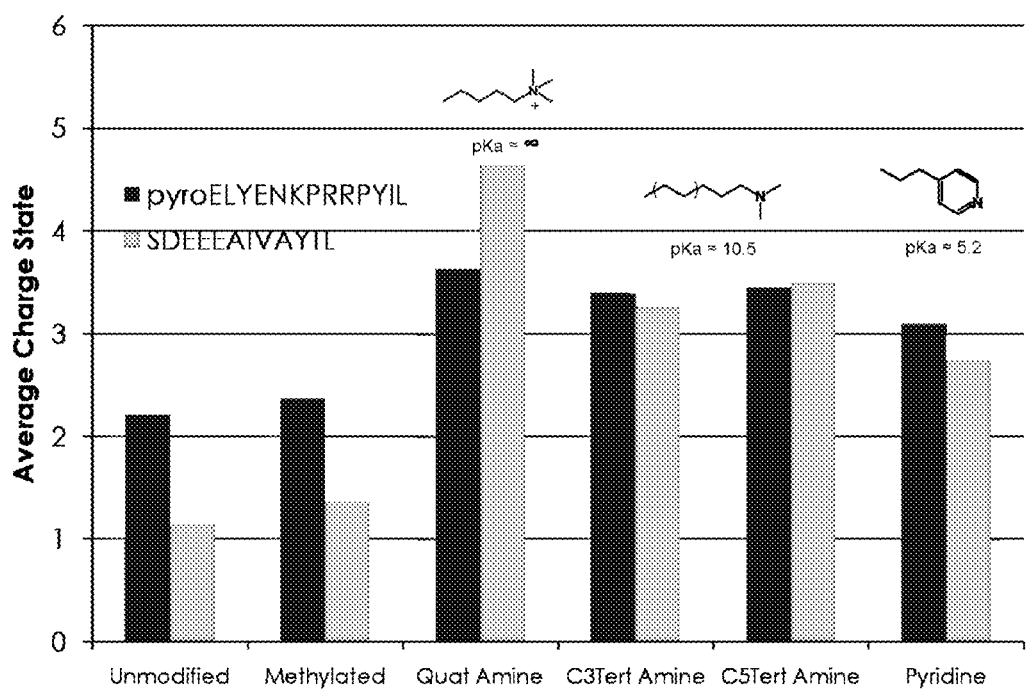
FIG. 5 shows the average charge state of two peptides (pyroELYENKPRRPYIL and SDEEEAIVAYTL) which are unmodified, amine-methylated, tagged with a quaternary amine, and tagged with various tertiary amines. The approximate pKa values of quaternary and tertiary amines are displayed.

One possible reason for the difference in average charge state between the tertiary amines may be related to the gas-phase basicity (or pKa if in a solution) of the tertiary amines. A tertiary amine having greater basicity would be expected to be more easily ionizable and therefore reach a higher charge state. FIG. 5 shows the average charge state of two peptides (pyroELYENKPRRPYIL and SDEEEAIVAYIL) unmodified, methylated, tagged with a quaternary amine, and tagged with different tertiary amines. The peptides tagged with the quaternary amine exhibited the highest charge state, while the unmodified and methylated peptides had the lowest charge states. The peptides tagged with the three different tertiary amines (C3tert amine, C5tert amine, and pyridine) had charge states less than the quaternary amine but greater than the unmodified peptides. In this experiment, the pKa value of the quaternary or tertiary amine group was predictive of the charge state relative to the other amine groups. The charged quaternary amine has a practically infinite pKa value and had the highest charge state. The C3tert and C5tert amines had a pKa value of approximately 10.5 and resulted in charge states less than the quaternary amine. Pyridine has a pKa value of approximately 5.2 and resulted in a charge state less than the C3tert and C5tert amines but still greater than the unmodified peptides.

Example 5

Chromatographic Separation of Tagged Peptides

Another problem encountered with labeling peptides with quaternary amines is that quaternary amines lead to reduced purification by chromatography. Preferably, a tagging reagent of the present invention is suitable for LC-MS/MS analysis, providing enhanced fragmentation while still allowing for effective separation by liquid chromatography. It is believed peptides tagged with tertiary amines will be better able to be purified by chromatography techniques.

Figure 6:
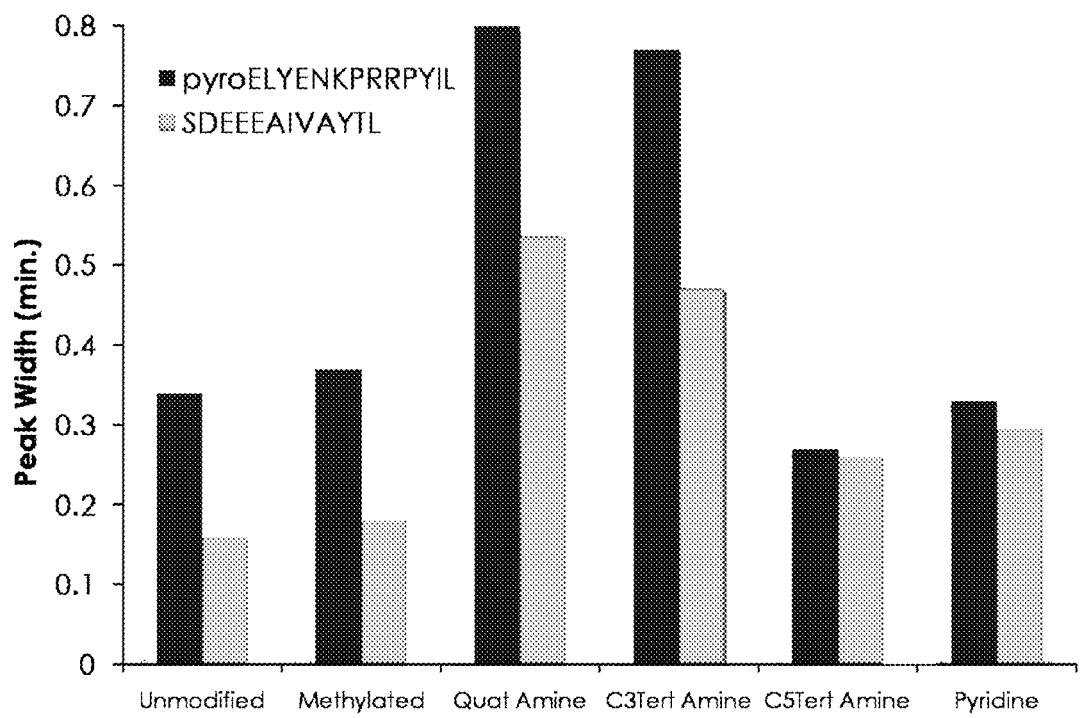
FIG. 6 illustrates the chromatographic separation of the tagged and unmodified peptides of FIG. 5.

FIG. 6 illustrates the chromatographic separation of the modified and unmodified peptides of FIG. 5 (pyroELYENK-PRRPYIL and SDEEEAIVAYIL). Approximately 2 pmol of each peptide was injected onto a 100×0.1 mm column packed with C18 stationary phase. The mobile phase was flowed at 50 µL/min and employed a biphasic gradient where mobile phase A was 0.1% formic acid in water, and mobile phase B was 0.1% formic acid in acetonitrile. The gradient was ramped from 0 to 30% B over 100 min., then 30 to 60% B over 40 min., then 60 to 100% B over 10 min, and then back to 0% B over 1 min. with a 15 min. equilibration time before the next run. As shown in FIG. 6, labeling the peptides with the quaternary amine resulted in a much broader peak width than the unmodified peptides. A narrower peak width indicates sharper separation during chromatography and is more desirable than a wider peak. One of the tertiary amines (C3tert amine) also resulted in a peak width significantly larger than the unmodified and methylated peptides. However, the other two tertiary amines (C5tert amine and pyridine) resulted in peak width comparable to the unmodified and methylated peptides and even narrower than the unmodified version of one of the peptides. All three tertiary amines had improved peak width compared to the quaternary amine indicating better separation.

Figure 7:
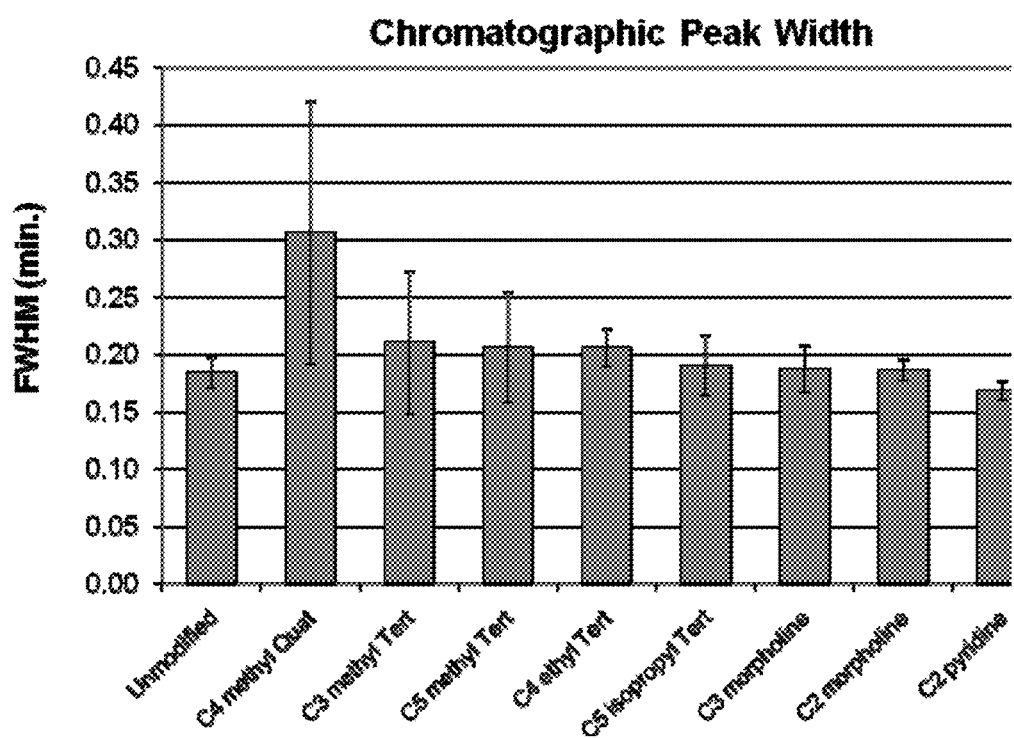
FIG. 7 shows the chromatographic peak widths of tagged and unmodified versions of a peptide (pyroELYENK-PRRPYIL).

Similarly, FIG. 7 illustrates chromatographic separation of modified and unmodified versions of a single peptide (pyroE-LYENKPRRPYIL) utilizing additional tagging reagents over multiple runs. A smaller chromatographic peak width, as measured by the full-width at half-maximum height (FWHM) shown on the y-axis of FIG. 7, indicates sharper separation during chromatography and is more desirable than a wider peak. The four alkyl tertiary amines, two morpholines, and the pyridine all exhibited narrower peaks compared to the quaternary amine indicating better separation.

Example 6

Electron Transfer Dissociation (ETD) Fragmentation of Tagged Peptides

Figure 8:
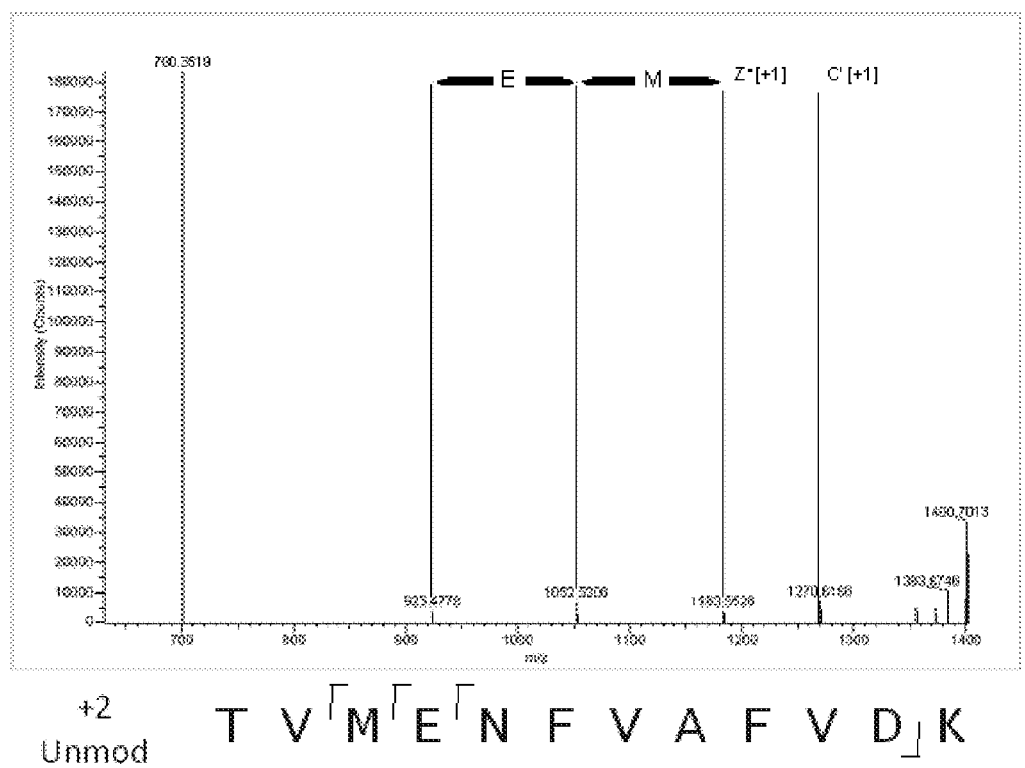
FIG. 8 shows an ETD fragmentation spectrum for an unmodified peptide (TVMENFVAFVDK) in the +2 charge state.
Figure 9:
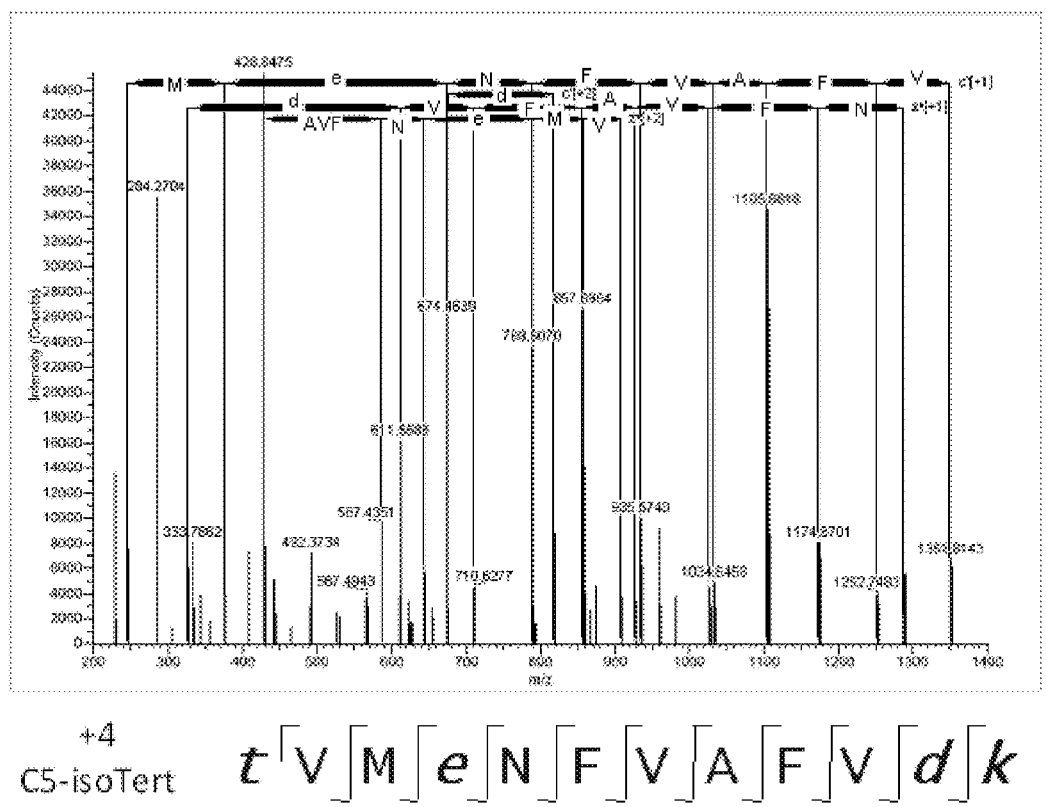
FIG. 9 shows an ETD fragmentation spectrum for the same peptide of FIG. 8 (TVMENFVAFVDK) but tagged with C5 isopropyl tertiary amine. The tagged protein is in the +4 charge state, and twenty-one out of twenty-two possible fragment ions are observed in the ETD spectrum.

FIGS. 8 and 9 show ETD fragmentation spectra for an unmodified and tagged peptide. FIG. 8 shows the ETD fragmentation spectrum for an unmodified peptide (TVMENFVAFVDK) in the +2 charge state. Only four out of a possible twenty-two fragment ions are observed. FIG. 9 shows the ETD spectrum for the same peptide modified with the C5 isopropyl tertiary amine tagging reagent. The tagged protein is in the +4 charge state, and twenty-one out of twenty-two possible fragment ions are observed in the ETD spectrum. These additional c and z fragment ions allow for more confident peptide identification.

Figure 10:
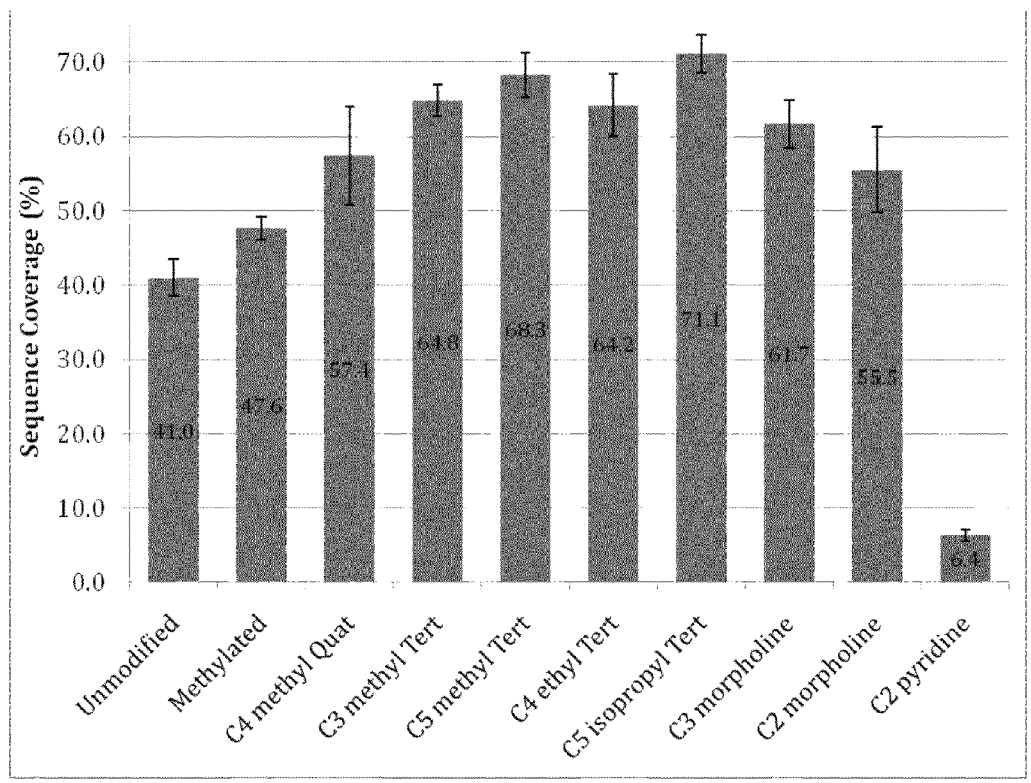
FIG. 10 shows the sequence coverage for BSA tryptic digests using unmodified peptides or peptides tagged with various reagents.

FIG. 10 shows the sequence coverage, i.e. the number of peptides identified with high confidence from an LC-MS run out of the total number of possible peptides, of unmodified peptides and tagged peptides using ETD fragmentation. Peptides generated from a BSA tryptic digest were left unmodified or labeled with various tagging reagents as described in Example 2. The peptides were then fragmented using ETD and analyzed using LC-MS. As shown in FIG. 10, the samples labeled with the four alkyl tertiary amines gave the highest results for sequence coverage. The C4 methyl quaternary amine and the two morpholine labeled samples yield better sequence coverage than the unlabeled tryptic digest, but not as good as the alkyl tertiary amines.

The C2 pyridine labeled digest sample provided poor peptide identification. This result is probably due to the heterocyclic aromatic pyridine group capturing the electron during ETD and then not transferring the electron to the peptide backbone. Consequently, backbone fragmentation is inefficient and the ETD spectra do not have many informative fragments for peptide identification. While the C2 pyridine tagging reagent was ineffective for ETD fragmentation in this example, pyridine tagging reagents were still able to increase the charge state of the peptide and may therefore be useful for methods other than ETD fragmentation.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional peptides, chemically modified peptides, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

The invention claimed is:

1. A method of ionizing and fragmenting a peptide having an amide backbone and one or more carboxylic acid groups comprising the steps of:
 a) providing the peptide;
 b) reacting at least a portion of the carboxylic acid groups of the peptide with a tagging reagent having a functional group having a greater gas-phase basicity than the amide backbone of the peptide, wherein the tagging reagent has the formula:

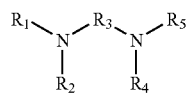

wherein,
 $R_1$ and $R_2$, independently of one another, are a hydrogen or a binding functional group which allows the binding functional group or a nitrogen attached to the binding functional group to react with a carboxylic acid;
 $R_3$ is selected from the group consisting of branched and unbranched alkylene groups having 1 to 10 carbon atoms, which are optionally substituted; and
 $R_4$ and $R_5$, independently of one another, are selected from the group consisting of hydrogen, and branched and unbranched alkyl groups having 1 to 10 carbon atoms, which are optionally substituted,
 wherein the tagging reagent and carboxylic acid groups react to link the functional group to the peptide to generate a labeled peptide, and wherein the functional group is not a nucleophile when the tagging reagent reacts with the carboxylic acid groups;
 c) ionizing the labeled peptide using electrospray ionization, thereby generating an ionized peptide, wherein the functional group of the labeled peptide increases the charge state of the ionized peptide compared to an unlabeled form of the peptide; and
 d) fragmenting the ionized peptide via electron transfer dissociation (ETD) or electron capture dissociation (ECD).

2. The method of claim 1 wherein the tagging reagent and carboxylic acid groups of the peptide react via an amidation reaction.

3. The method of claim 1 wherein the tagging reagent and carboxylic acid groups react to link from 1 to 10 functional groups to the peptide wherein said functional groups have a greater gas-phase basicity than the amide backbone of the peptide.

4. The method of claim 1 further comprising chemically blocking at least a portion of cysteine residues in the peptide, and chemically blocking at least a portion of lysine residues and the N-terminus of the peptide, prior to reacting at least a portion of the carboxylic acid groups of the peptide with the tagging reagent.

5. The method of claim 1 comprising fragmenting the ionized peptide via electron transfer dissociation (ETD).

6. The method of claim 1 wherein reacting carboxylic acid groups of the peptide with the tagging reagent has a yield of tagged peptide of approximately 90% or greater.

7. The method of claim 1 wherein the functional group of the tagging reagent is an aliphatic tertiary amine.

8. The method of claim 1 wherein the functional group of the tagging reagent is selected from the group consisting of protected primary or secondary amines.

9. The method of claim 8 further comprising the step of removing a protecting group from the primary or secondary amines after reacting the carboxylic acid groups of the peptide with the tagging reagent and prior to ionizing or fragmenting the peptide.

10. The method of claim 1 further comprising digesting a peptide precursor with trypsin, chymotrypsin, Lys-C, Glu-C, Asp-N, Arg-C, pepsin, cyanogen bromide, or nitro-thiocyanobenzoic acid (cys NTCB), thereby generating the peptide having one or more carboxylic acid groups.

11. The method of claim 1 wherein the tagging reagent is isotopically labeled.

12. The method of claim 11 wherein the tagging reagent contains deuterium, $^{13}C$, $^{15}N$, or $^{18}O$.

13. The method of claim 11 further comprising reacting at least a portion of the carboxylic acid groups of the peptide with an isotopically labeled tagging reagent (a heavy tag) and comparing said isotopically labeled peptide with a peptide tagged with a tagging reagent that is not isotopically labeled (a light tag).

14. The method of claim 1 further comprising purifying the peptide or a peptide precursor from a mixture.

15. The method of claim 14 wherein the mixture is a cell lysate.

16. A method of analyzing a peptide having an amide backbone and one or more carboxylic acid groups comprising the steps of:
 a) providing the peptide;
 b) reacting at least a portion of the carboxylic acid groups of the peptide with a tagging reagent having a functional group having a greater gas-phase basicity than the amide backbone of the peptide, wherein the tagging reagent has the formula:

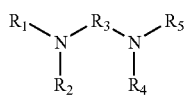

wherein,
- $R_1$ and $R_2$, independently of one another, are a hydrogen or a binding functional group which allows the binding functional group or a nitrogen attached to the binding functional group to react with a carboxylic acid;
- $R_3$ is selected from the group consisting of branched and unbranched alkylene, groups having 1 to 10 carbon atoms, which are optionally substituted; and
- $R_4$ and $R_5$, independently of one another, are selected from the group consisting of hydrogen, and branched and unbranched alkyl groups having 1 to 10 carbon atoms, which are optionally substituted, wherein the tagging reagent and carboxylic acid groups react to link the functional group to the peptide, thereby generating a labeled peptide, and wherein the functional group is not a nucleophile when the tagging reagent reacts with the carboxylic acid groups;

c) ionizing the labeled peptide using electrospray ionization, thereby generating an ionized peptide, wherein the functional group of the labeled peptide increases the charge state of the ionized peptide compared to an unlabeled form of the peptide;

d) fragmenting the ionized peptide via electron transfer dissociation (ETD) or electron capture dissociation (ECD); and e) analyzing fragments of the ionized peptide.

17. The method of claim 16 wherein fragmenting the ionized peptide is achieved via electron transfer dissociation (ETD).

18. The method of claim 16 further comprising identifying one or more fragments of the ionized peptide using mass spectrometry.

19. The method of claim 18 further comprising quantifying amounts of said one or more fragments of the ionized peptide.

20. The method of claim 1 wherein $R_4$ and $R_5$, independently of one another, are alkyl groups having 1 to 3 carbon atoms.

21. The method of claim 1 wherein $R_3$ is an alkylene group having 2 to 5 carbon atoms.

22. The method of claim 16 wherein $R_3$ is an alkylene group having 2 to 5 carbon atoms and $R_4$ and $R_5$, independently of one another, are alkyl groups having 1 to 3 carbon atoms.

* * * * *